United States Patent [19]

Campbell

[11] Patent Number: 5,118,688
[45] Date of Patent: Jun. 2, 1992

[54] TETRAHYDROPYRIDOQUINOLONE DERIVATIVES USEFUL AS ANXIOLYTIC AGENTS

[75] Inventor: James B. Campbell, Chadds Ford, Pa.

[73] Assignee: ICI Americas Inc., Wilmington, Del.

[21] Appl. No.: 583,070

[22] Filed: Sep. 14, 1990

Related U.S. Application Data

[62] Division of Ser. No. 43,873, Apr. 29, 1987, Pat. No. 4,975,435.

[30] Foreign Application Priority Data

May 6, 1986 [GB] United Kingdom ............... 8610980

[51] Int. Cl.$^5$ .................... C07D 471/04; A61K 31/44
[52] U.S. Cl. .................................... 514/292; 546/81; 546/82; 546/84; 546/88
[58] Field of Search .................... 546/81, 88; 514/292

[56] References Cited

U.S. PATENT DOCUMENTS

| | | | |
|---|---|---|---|
| 3,647,800 | 3/1972 | Wolf et al. | 546/81 |
| 3,853,880 | 12/1974 | Challier et al. | 514/255 |
| 4,450,167 | 5/1984 | Le Martret et al. | 514/311 |
| 4,511,568 | 4/1984 | Bare et al. | 514/293 |
| 4,546,104 | 10/1985 | Campbell, Jr. et al. | 514/293 |
| 4,631,286 | 12/1986 | Shutske et al. | 514/297 |
| 4,705,793 | 11/1987 | Resch | 514/293 |

FOREIGN PATENT DOCUMENTS 0205362 12/1986 European Pat. Off. ............ 514/311

*Primary Examiner*—Alan L. Rotman
*Attorney, Agent, or Firm*—Rosemary M. Miano; Thomas E. Jackson

[57] ABSTRACT

The present invention comprises certain quinoline lactams of formula I; pharmaceutically acceptable salts of the compounds of formula I; pharmaceutical compositions containing a compound of formula I, or a pharmaceutically acceptable salt thereof, for use in the treatment of anxiety; and processes for the manufacture of the compounds of formula I, as well as intermediates for use in such manufacture.

8 Claims, No Drawings

TETRAHYDROPYRIDOQUINOLONE DERIVATIVES USEFUL AS ANXIOLYTIC AGENTS

This is a divisional application of co-pending application Ser. No. 07/043,873 filed on Apr. 29, 1987 and now U.S. Pat. No. 4,975,435.

SUMMARY OF THE INVENTION

The compounds of the invention are heterocyclic fused tricyclics with selected side chain substitutions on the A and C rings, which are useful as agents for binding to benzodiazepine receptors, and which may also be used as biochemical tools.

DETAILED DESCRIPTION OF THE INVENTION

Selected tricyclic compounds described as memory enhancers are described in EPO Publication No. 0,179,383 to Shutske et al. Selected tricyclic pyrazolopyridines are disclosed in U.S. Pat. Nos. 4,511,568 to Bare et al and 4,546,104 to Campbell et al (both of which are assigned to the same assignee as this application). Quinoline compounds may be seen in EPO Publications Nos. 0,205,362 to Keane et al and 0,070,767 to Le Martret and Le Martret et al U.S. Pat. No. 4,450,167.

The compounds of the invention are tricyclics of formula I:
(Formula set out on pages following Examples) I
where ring A is a 5 or 6 membered aromatic ring selected from the group consisting of the members shown in formulae Ia-Ie:
(Formulae set out on pages following Examples) Ia, Ib, Ic, Id, Ie
wherein:
n = 1 or 2;
X = >C—H or N;
Y = O, S, or >N—Rd; and
where > indicates two bonds;

Ra is selected from a group consisting of (1-10C)alkyl, (3-10C)alkenyl, (3-10C)-alkynyl, (3-7C)cycloalkyl, (4-7C)cycloalkenyl, (4-10C)cycloalkylalkyl, (5-9C)alkylidenecycloalkylalkyl, (1-4C)alkoxy, (1-4C)alkylthio, (2-10C)hydroxyalkyl, (4-10C)hydroxycycloalkylalkyl, (2-10C)ketoalkyl, (1-10C)haloalkyl and (3-10C)haloalkenyl having at least one halo group wherein the halo group(s) is independently selected from a group consisting of fluoro and chloro, (6-10C)aryl, (7-12C)arylalkyl (wherein said aryl portion of the aryl or arylalkyl may, optionally, be substituted by a member selected from a group consisting of (1-4C)alkyl, (1-4C)alkoxy, halogeno, and amino optionally substituted independently by one or two of (1-4C)alkyl), and wherein the alkyl portion of the arylalkyl may optionally be substituted by hydroxy, a heteroaryl having a 5 or 6-membered ring wherein said ring contains one or more heteroatoms independently selected from a group consisting of sulfur, oxygen and nitrogen and wherein the heteroaryl may optionally be substituted by (1-3C)alkyl, a heteroaryl(1-3C)alkyl having a 5 or 6-membered ring wherein said ring contains 1-3 heteroatoms independently selected from a group consisting of sulfur, oxygen and nitrogen and wherein the heteroaryl may optionally be substituted by (1-3C)alkyl;

Rb is selected from a group consisting of hydrogen, (1-10C)alkyl (optionally substituted by (1-3C)al-koxy), (3-7C)-cycloalkyl, (4-10C)cycloalkylalkyl, (3-8C)alkenyl, (3-8C)alkynyl, (2-8C)haloalkyl having 1-3 halo group(s) independently selected from fluoro and chloro, (2-8C)haloalkenyl having 1-3 halo group(s) independently selected from fluoro and chloro, (2-8C)hydroxyalkyl, phenyl, phenyl(1-3C)alkyl, (wherein the phenyl portion of phenyl or phenylalkyl is optionally substituted by a member selected from a group consisting of halogeno, (1-3C)alkyl and (1-3C)alkoxy), a 5 or 6 membered heteroaryl or heteroaryl(1-3C)alkyl, containing 1, 2, or 3 members selected independently from a group consisting of sulfur, oxygen and nitrogen, wherein the aryl portion of the aryl or arylalkyl may optionally be substituted by (1-3C)alkyl;

Rc is selected from a group consisting of hydrogen, (1-10C)alkyl and (2-10C)alkanoyl;

Rd is independently selected from the group defined for Rc;

and salts, for example and especially pharmaceutically acceptable salts thereof.

Particular values for Ra include (1-6C)alkyl, (3-7C)cycloalkyl, (4-7C)cycloalkenyl, (4-8C)cycloalkylalkyl, (1-4C)alkoxy, (1-4C)alkylthio, (3-6C)al-kenyl, (3-6C)alkynyl, (6-10C)-aryl, (7-12C)-arylalkyl (wherein the aryl portion of the aryl or arylalkyl may optionally be substituted by (1-3C)alkyl, (1-3C)alkoxy, halogeno, or amino optionally substituted independently by 1 or 2 of (1-3C)alkyl, and wherein the alkyl portion of the arylalkyl may optionally be substituted by hydroxy); (1-6C)haloalkyl having at least one of fluoro or chloro, (3-6C) hydroxyalkyl (4-8C)hydroxycycloalkylalkyl, a 5 or 6membered heteroaryl or substituted heteroaryl having 1 or 2 heteroatoms (wherein the substitution is (1-3C)alkyl), a 5 or 6-membered ring heteroarylalkyl having 1 or 2 heteroatoms, optionally substituted by (1-3C)alkyl.

Particular values for Rb include (2-5C)alkyl optionally substituted by (1-3C)alkoxy, (3-5C)alkenyl, (3-5C)alkynyl, (4-6C-)cycloalkylalkyl, (3-5C)haloalkenyl having 1-3 halo group(s), phenyl, phenyl(1-3C)alkyl, (wherein the phenyl portion of phenyl or phenylalkyl is optionally substituted by a member selected from a group consisting of halogeno, (1-3C)alkyl and (1-3C)alkoxy), a 5 or 6 membered heteroaryl or heteroaryl(1-3-C)alkyl, containing 1 or 2 members selected independently from a group consisting of sulfur, oxygen and nitrogen, wherein the aryl portion of the aryl or arylalkyl may optionally be substituted by (1-3C)alkyl;

Particular values for Rc include hydrogen, (1-6C)alkyl and (2-6C)alkanoyl.

A particular value for Rd is hydrogen.

More particular values for compounds of formula I include those where A is selected from formula Ia, Ib, Ic and Id, preferably Ia.

More particular values for Ra include (1-6)alkyl, (4-8C)cycloalkylalkyl, (3-6C)alkenyl, (3-6C)alkynyl, phenyl, phenyl(1-2C)alkyl (wherein the phenyl or phenyl portion of the phenylalkyl may optionally be substituted by a member selected from a group consisting of fluorine, chlorine, bromine, methyl, ethyl, propyl, methoxy, ethoxy, propoxy, and amino optionally substituted independently by 1 or 2 of (1-3C)alkyl, and wherein the alkyl portion of the phenylalkyl may optionally be substituted by hydroxy), heteroarylalkyl selected from a group consisting of 2-thienylmethyl, 3-thienylmethyl, N-methyl-2-pyrrolylmethyl, 2-thiazolylmethyl, 2-oxazolylmethyl, 3-pyridylmethyl and 4-pyridylmethyl.

More particular values for Rb include (2–5C)alkyl optionally substituted by (1–3C)alkoxy, (3–5C)alkenyl, (3–5C)alkynyl, (4–6C)cycloalkylalkyl, benzyl optionally substituted on the phenyl by a member selected from a group consisting of fluorine, chlorine, bromine, (1–3C)alkyl and (1–3C)alkoxy: and a heteroalkylalkyl selected from 2-furylmethyl.

More particular values for Rc include hydrogen, propyl, butyl, acetyl, butyryl and valeryl.

Even more particular values for the above described groups are as follows:

Ra: methyl, ethyl, n-propyl, n-butyl, 3-methylbutyl, n-pentyl, 2-methylbutyl, 2,2-dimethylpropyl, 2-methylpropyl, 3-trifluoromethylbutyl, 4,4,4-trifluorobutyl, 1-hydroxy-3-methylbutyl, 1-hydroxypropyl, 3-butenyl, 1-propenyl, 2-propenyl, 2-methyl-1-propenyl, 3-pentynyl, cyclopropylmethyl, cyclopentylmethyl, cyclohexylmethyl, 2-thienylmethyl, 3-thienylmethyl, benzyl, phenethyl, 4-fluorobenzyl, 1-hydroxy-1-phenylmethyl, phenyl, 4-chlorophenyl, 4-fluorophenyl, 4-methoxyphenyl, 4-methylphenyl, 3-methoxyphenyl, 2-methoxyphenyl, 4-dimethylaminophenyl;

Rb: ethyl, n-propyl, n-butyl, 2-methoxyethyl, 3-methoxypropyl, 2-propenyl, 2-propynyl, 2-butynyl, cyclopropylmethyl, benzyl, 2,4-dimethoxybenzyl, 3-chlorobenzyl, 4-fluorobenzyl, 4-methoxybenzyl, 4-chlorobenzyl, 3-methoxybenzyl, 2-fluorobenzyl and 2-furylmethyl:

Rc: hydrogen: and these compounds are further useful as anxiolytics.

Preferably compounds of formula I are selected to be those wherein X=nitrogen and n=1. Rb is preferably chosen to be propyl, butyl or 2-propenyl.

Preferred compounds of the invention are those of formula I as follows: (a) A is selected as formula Ia with n=1, X=nitrogen, Ra=3-methylbutyl, Rb=propyl and Rc=hydrogen: (b) A is selected as formula Ia with n=1, X=nitrogen, Ra=2-methylpropyl, Rb=propyl and Rc=hydrogen: (c) A is selected as formula Ia with n=1, X=nitrogen, Ra=cyclopropylmethyl, Rb=propyl and Rc=hydrogen: and most preferably (d) A is selected as formula Ia with n=1, X=nitrogen, Ra=-propyl, Rb=propyl and Rc=hydrogen.

It will be appreciated that certain of the compounds of this invention may contain an asymmetrically substituted carbon atom, and may exist in, and be isolated in, optically-active and racemic forms. In addition, it will be appreciated that certain compounds of this invention may exist in and be isolated in, separate stereoisomeric forms ('E' and 'Z') about that group. Some compounds may exist in more than one tautomeric form. Some compounds may exhibit polymorphism. It is to be understood that the present invention encompasses any racemic, optically-active, tautomeric, polymorphic or stereoisomeric form, or mixtures thereof, which form possesses benzodiazepine binding properties, it being well known in the art how to prepare optically-active forms (for example, by resolution of the racemic form or by synthesis from optically-active starting materials) and individual 'E' and 'Z' stereoisomers (for example, by chromatographic separation of á mixture thereof) and how to determine the benzodiazepine binding properties by the standard tests described hereinafter.

In this specification Ra, Rb, et cetera stand for generic radicals and have no other significance. It is to be understood that the generic term "(1–6C)alkyl" includes both straight and branched chain alkyl radicals but references to individual alkyl radicals such as "propyl" embrace only the straight chain ("normal") radical, branched chain isomers such as "isopropyl" being referred to specifically. A similar convention applies to other generic groups, for example, "alkylene" and "alkenylene" et cetera. Halogeno or halo is fluoro, chloro, or bromo.

The salts of the compounds of formula I are preferably the pharmaceutically acceptable salts, but other salts may, for example, find use in the preparation of the compounds of formula I and the pharmaceutically acceptable salts thereof.

A particular pharmaceutically acceptable acid addition salt is one formed with hydrochloric, hydrobromic, sulfuric, nitric, phosphoric acid or methane sulfonic acid.

Compounds of formula I may be prepared by using methods known in part for the preparation of chemically similar compounds. Thus the following processes are provided as a further feature of the invention:

(a) Compounds of formula I in which Rc is hydrogen may be prepared by cyclization of a compound of formula II:

(Formula set out on pages following Examples) II for example, in a manner similar to that described in U.S. Pat. Nos. 4,511,568 and 4,546,104 using cyclization catalysts which may include $(CH_3)_3Al$, $CuO_2CCH_3$, $ZnCl_2$, $ZnBr_2$, $NaH/CdCl_2$ and at a temperature of ambient to 120°.

(b) Compounds of formula I, in which A is selected from formula Ia, Ib and Ic and in which Rc is hydrogen and Ra is a group of formula $CH_2Re$ (where Re has the value as defined below), may be prepared by alkylation and cyclization, for example in a sequential single pot alkylation-cyclization, of a compound of formula IIa, (Formula set out on pages following Examples) IIa which $A^1$ has the values as defined for A except that Ra=—$CH_2Cl$, by reaction with an alkylating agent $(Re)_pM$, preferably at about 0° to ambient temperature for the alkylation step, preferably followed by heating to about 40°–70° to effect cyclization. Re is selected from a group defined for Ra in which a —$CH_2$— has been removed at the point of attachment to the A ring and provided that Re must be selected so that it is possible to remove a —$CH_2$—; thus Re may not be selected to be from those defined for Ra such as aryl, heteroaryl, cycloalkyl, alkenyl or alkynyl where the multiple bond is on the carbon attached to the A ring, et cetera: M is selected from a group consisting of zinc, cadmium and titanium: p has a value of 2 when M=Zn or Cd and a value of 4 when M=Ti:

(c) For those compounds of formula I, where A=formula Ia in which Ra is, for example, alkyl, alkenyl, alkynyl, cycloalkyl, cycloalkenyl, (cycloalkyl)alkyl, aryl, (aryl)alkyl, or substituted aryl (where substitution is alkyl, halogeno, alkoxy, or dialkylamino), these compounds may be made by reacting an organometallic derivative of the compound RaX in which X is a halogen (for example an organozinc reagent), with that compound of formula I where A=formula Ia in which Ra is initially bromine or iodine, preferably at about ambient to 70° C., in the presence of a suitable transition metal catalyst (for example, dichloro[1,1'-bis(diphenylphosphino)ferrocene]palladium (II)).

Compounds of formula I in which Rc is hydrogen, A is of formula Ia and Ra is alkyl, alkenyl, alkynyl, cycloalkyl, cycloalkenyl, (cycloalkyl)alkyl, aryl, or substituted aryl, may be prepared by the deprotection of a compound corresponding to a compound of formula I, but in which NHRc is replaced by NHP in which P represents an amine protecting group. The protecting group is preferably a trifluoroacetyl group which may be removed by the use of a base as described herein. A protecting group may be used, for example, in certain cases milder reaction conditions may be employed by first reacting compounds of the formula I where A = -formula Ia in which Ra is initially bromine or iodine, with trifluoroacetic anhydride in the presence of a base such as sodium hydride. The resulting N-trifluoroacetylated compound may then be reacted with an organometallic derivative of compound RaX in which X is a halogen (for example an organozinc reagent) at ambient temperature in the presence of a suitable transition metal catalyst such as those described above. The resulting compound (after treatment with base in alcohol) (for example KOH in methanol) gives the substituted compounds of formula I where A = formula Ia.

(d) For those compounds of formula I where A is formula Ia in which Ra is 1-hydroxyalkyl or 1-hydroxyaryl, these compounds may be made by reacting an organometallic derivative of formula ReX in which X is a halogen (for example organolithium or a Grignard reagent) with a compound of the formula I where A is formula Ia and Ra is formyl. Compounds of formula I where A is formula Ia and Ra is formyl may be prepared by ozonolysis of compounds where Ra is 1-alkenyl.

(e) Compounds of formula I in which A is selected to be formula Ib with Y = S and Rc = hydrogen may be prepared by reaction of a compound of formula III:

(Formula set out on pages following Examples) III where Z is chloro or ethoxy with ammonia:

(f) Compounds of formula I in which Rc is alkanoyl may be prepared by acylation of a compound of formula I in which Rc is hydrogen: and (g) Compounds of formula I in which Rc is alkyl may be prepared by alkylation of a compound of formula I in which Rc is hydrogen.

Process (a) is the preferred method for synthesis of compounds of formula I. The starting material of formula II for process (a) may be prepared by condensation of the appropriate aminonitrile of formula IV:

(Formula set out on pages following Examples) IV with a compound of formula V:

(Formula set out on pages following Examples) V

The compounds of formula V when X = N may be made as described in U.S. Pat. No. 4,511,568 (See the description of compound XIV contained therein.) The compounds of formula V when X = >C—H may be made as described in U.S. Pat. No. 4,546,104 (see the description of compound III contained therein.)

Compounds of formula IV where A is selected to be formula Ia may be prepared according to the procedures described by Marvel, et al, *Org. Synthesis, Collect. Vol. I*, page 327 (1951), and Bedford et al, *J. Chem. Soc.*, pages 1633-1634 (1959).

Compounds of formula IV where A is selected to be formula Ia may also be prepared according to an improved variation of the synthesis described by Bedford et. al. (supra). Thus, treatment of the isatin oximes described by Bedford with trifluoromethanesulfonic anhydride in the presence of a hindered amine base, for example, 2,6-lutidine, followed by addition of a bicyclic amidine base, for example, 1,8-diazabicyclo[5.4.0]undec-7-ene then hydrolysis in dilute aqueous base (for example, sodium bicarbonate), all at ambient temperature, gives compounds of the formula IV where A is selected to be formula Ia.

Compounds of formula IV where A is selected to be formula Ia in which Ra is, for example, alkyl, alkenyl, alkynyl, cycloalkyl, cycloalkenyl, (cycloalkyl)alkyl, aryl, (aryl)alkyl, substituted aryl (where substitution is alkyl, halogeno, alkoxy or dialkylamino) may be made by reacting an organometallic derivative of formula RaX in which X is a halogen (for example an organozinc reagent) with that compound of formula IV where A is formula Ia in which Ra is initially iodine, in the presence of a suitable transition metal catalyst (for example, dichloro[1,1'-bis(diphenylphosphino)ferrocene]palladium (II)).

Compounds of formula IV where A is selected to be formula Ia and where Ra is methyl, may be prepared from commercially available 3-methyl-2nitrobenzoic acid by first converting it to the amide, then dehydrating the amide to the nitrile with subsequent reduction of the nitro group.

Compounds of formula IV where A is selected to be formula Ic and where Y is >N-Rd may be prepared using the procedure described by Klein et al, Tet. Letters, 22: 25-28 (1981).

Compounds of formula IV where A is selected to be formula Id may be prepared using the procedure described by Yamazaki et al, *Chem. and Pharm. Bull.*, 30: 2357-2363 (1982).

A second method for the preparation of the starting material of formula II where A is selected to be formula Ia comprises a novel process. Thus, 3-methyl-2-nitrobenzonitrile is converted by oxidation of the methyl group to the aldehyde. Subsequent reduction to the 3-(hydroxymethyl)-2-aminobenzonitrile gives an intermediate of formula IV where Ra is hydroxymethyl and A is selected to be formula Ia. Condensation with a compound of formula V followed by conversion of hydroxy to chloro generates the intermediate of formula IIa. Alkylation of compounds of formula IIa may be effected using diorganozinc or diorganocadmium reagents of formula $(Re)_pM$ at or below ambient temperature in an inert solvent such as methylene chloride to give compounds of formula II where Ra is an alkyl group.

The diorganozinc reagents may be prepared according to literature procedures employing, for example, either Grignard reagents or organolithium reagents and anhydrous zinc halide, for example, zinc bromide. (See Houben-Weyl, *Method. der Organischen Chemie*, George Thieme, Volume 13/2a (1973)).

Condensation of methyl 4-amino-5-alkylthiophene-3-carboxylate of formula VI with cyclic 1,3-dicarbonyl compounds of formula V, followed by base-catalyzed ring closure affords thieno-tricyclic compounds of formula VII (Formula set out on pages following Examples) VII where W = OH. These thieno-tricyclics may be converted with $SOCl_2$/dimethyl formamide to compounds of formula III where Z is chloro or with base and ethyl iodide or ethyl bromide to compounds of formula III where Z is ethoxy.

Compounds of formula III for use in process (e) may be made as follows:

Methyl 4-amino-5-alkylthiophene carboxylates of formula VI (Formula set out on pages following Examples) VI may be prepared as described in U.S. Pat. No. 4,317,915. Thus, compounds of formula VI with Ra as propyl (69% yield), butyl (68% yield) and pentyl (47% yield) were prepared.

Pharmaceutically acceptable acid addition salts may be formed by reacting a compound of formula I with an appropriate acid, for example, by dissolving a compound of formula I in a suitable solvent, adding a selected acid to the solution and recovering the salt. It may be desired to optionally use a protecting group during all or portions of the above described processes: the protecting group then may be removed at the appropriate time.

As indicated above, the compounds of the present invention are useful as binders to benzodiazepine receptors. This may be demonstrated by using a tritiated flunitrazepam binding assay (FNB test) (see U.S. Pat. Nos. 4,511,568 and 4,546,104.) Compounds capable of binding to benzodiazepine receptors are known to possess a spectrum of activities which range from anxiolytic activity to the activity of reversing the action of benzodiazapines in the central nervous system. In general, the compounds of the present invention are believed to possess anxiolytic activity. It will be appreciated, however, that compounds will vary in their activity depending on chemical structure and, thus, compounds of the present invention will possess a varying ratio of such above mentioned activities. Anxiolytic activity may be demonstrated in the Shock-Induced Suppression of Drinking (Rats) Test (SSD) described in *Pharmacology Biochemistry and Behavior*, 12: 819-821 (1980). This test may be carried out as follows:

Male rats in the weight range of 200 to 220 g are deprived of water for 48 hours and deprived of food for 24 hours before testing. Normally, the rats are orally intubated and receive a volume of 5 ml/kg containing the appropriate concentration of test compound (based on mg/kg body weight) in a vehicle of hydroxypropylmethylcellulose (HPMC) 0.5% w/v, polyoxyethylene (20) sorbitan monooleate (Tween 80) 0.1% w/v, and distilled water. The vehicle control group of rats is also intubated by mouth. A positive control group of rats is orally administered a control dose of 18 mg/kg of chlordiazepoxide. Random selection of the rats is utilized in dosing. The rats are returned to the cage for one hour. Sixty minutes after drug administration, the rat is quietly removed from its cage and the hind feet wiped with Signa electrode gel made by Parker Laboratories of Orange, New Jersey. When intraperitoneal (i.p.) administration is used, the protocol is identical except that the drugs are administered in varying concentrations in saline in a volume of 5 ml/kg 30 minutes prior to testing. Concentrations ranged from 0.4 to 50 mg/kg The rat is placed on the floor in the chamber facing the licking tube. The animal is allowed 5 minutes to make 20 licking responses and receive the first shock (0.5 mA). If this response does not occur, the animal is removed and eliminated from the study. If 20 licking responses are made, the animal is permitted an additional 3 minutes during which time each 20th lick is paired with a 0.5 mA shock. This period is automatically started, counted and terminated. The number of licks and shocks are recorded. The activity of the compound tested is evaluated by comparing the mean shocks of the group dosed with the test compound to both the mean shocks of the vehicle and positive control groups via a Students' t-test. In general, an increase in the number of shocks received compared to the control is indicative of the anti-conflict or anti-anxiety activity of the compound.

Representative compounds of the present invention typically show results in the SSD test indicative of anxiolytic activity.

According to a further feature of the invention there is provided a pharmaceutical composition which comprises a tricyclic derivative of the invention in association with a pharmaceutically-acceptable diluent or carrier.

The pharmaceutical composition may, for example, be in a form suitable for oral, rectal or parenteral administration, for which purposes it may be formulated by means known to the art into the form of, for example, tablets, capsules, aqueous or oily solutions or suspensions, emulsions, dispersible powders, suppositories or sterile injectable aqueous or oily solutions or suspensions.

A preferred pharmaceutical composition of the invention is one suitable for oral administration in unit dosage form, for example a tablet or capsule which contains between 0.1 mg and 500 mg of the tricyclic derivative, or one suitable for intravenous, intramuscular or subcutaneous injection; for example, a sterile injectable containing between 0.1% and 10% w/w of the tricyclic derivative.

The pharmaceutical composition of the invention will normally be administered to mammals such as man for relief of anxiety and tension in the same manner as that employed for chlordiazepoxide, due allowance being made in terms of dose levels for the potency and duration of actions of the tricyclic derivative of the invention relative to chlordiazepoxide. Thus each individual, will receive an oral dose of between 0.5 mg and 500 mg, and preferably between 0.5 mg and 20 mg, of tricyclic derivative, or an intravenous, subcutaneous or intramuscular dose of between 0.5 mg and 100 mg, and preferably between 0.5 mg and 20 mg, of the tricyclic derivative, the composition being administered one to four times per day. The rectal dose will be approximately the same as the oral dose.

The invention is illustrated but not limited by the following examples in which temperatures are in degrees Celsius and ambient temperature refers to $23° \pm 3°$. Chemical symbols have their usual meanings unless otherwise specified and the following abbreviations are used: ml (milliliter), g (gram), mg (milligram), m.p. (melting point), tlc (thin layer chromatography), $R_f$ (relative mobility in tlc), atmospheric pressure ($1.013 \times 10^5$ Pascals/atm), hr. (hour), min. (minute), Ra, Rb etc. are generic radicals and have the meanings stated above unless indicated otherwise. Unless stated otherwise, ratios of solvents are by volume/volume, v/v.

In general, no sign of overt toxicity has been observed with compounds of the invention at dosages at least several multiples of their minimum effective doses in the SSD test.

EXAMPLE 1 a.

9-Amino-2,3-dihydro-5-methyl-2-propylpyrrolo[3,4-b]quinolin-1-one (Formula I, A=formula Ia, X=N, n=1, Ra=methyl, Rb=propyl, Rc=H)

The benzonitrile described in Example 1e (0.60 g) was suspended in methylene chloride (10 ml) maintained at ice bath temperature under an argon atmosphere. Trimethylaluminum (3.48 ml of a 1.35 M solution in heptane) was added dropwise to the reaction vessel. After the addition was completed the cooling bath was removed and the solution was warmed to ambient temperature then heated to gentle reflux (about 45°). After heating for 4 hours at reflux, the reaction solution was cooled in an ice bath and carefully quenched by adding water dropwise. The mixture was made basic (pH greater than 9) with 10% aqueous NaOH, then ethyl acetate/tetrahydrofuran was added. The organic phase was separated and successively washed with brine, dried ($Na_2SO_4$) and concentrated. The crude product was chromatographed over silica gel using ethyl acetate:hexane (3:7) as the eluent. The resulting white solid was recrystallized from acetone/hexane to give the title compound as a white solid (210 mg, 35%): m.p. 200-207° (with decomposition): tlc, $R_f=0.28$, silica gel, ethyl acetate:hexane (1:1): a small impurity was evident at $R_f=0.50$.

Analysis calculated for $C_{15}H_{17}N_2O$: C, 70.56: H, 6.71: N, 16.45. Found: C, 69.51: H, 6.69: N, 16.09.

b. 3-Methyl-2-nitrobenzenecarboxamide

To a solution of 3-methyl-2-nitrobenzoic acid (13.2 g) in tetrahydrofuran (150 ml) was added slowly at ambient temperature triethylamine (11.0 ml). After stirring for 30 minutes, the solution was cooled in an ice bath and ethyl chloroformate (7.6 ml) was added dropwise. Following the addition the thick mixture was stirred for 1 hour while maintaining the temperature at about 0°. Next, gaseous ammonia was bubbled through the well stirred mixture until it was well saturated (about 15 minutes). The cooling bath was removed and the mixture was allowed to warm slowly to ambient temperature with stirring for 2 hours. The mixture was partitioned between ethyl acetate and water; some gentle warming was required to solubilize all of the solid material. The layers were separated: the organic phase was washed with brine, dried over $Na_2SO_4$ and concentrated to leave a white solid. Trituration with ether/hexane followed by filtration afforded the carboxamide (12.5 g, 95%): m.p. 189°-191°; tlc, $R_f=0.08$, silica gel, ethyl acetate:hexane (1:1).

c. 3-Methyl-2-nitrobenzonitrile

To a mixture of the carboxamide of Example 1b (12.5 g) and pyridine (11.2 ml) suspended in tetrahydrofuran (100 ml) and maintained at ice bath temperature was added dropwise trifluoroacetic anhydride (10.7 ml) over a period of 30 minutes. After the addition, the resulting solution was warmed to ambient temperature and stirred for 3 hours. After removing the volatiles under aspirator vacuum, the remaining crude solid was partitioned between equal volumes of ethyl acetate and water. The layers were separated: the ethyl acetate layer was washed with brine, dried over $MgSO_4$ and filtered through a small pad of silica gel. After concentrating the material, the resulting solid was recrystallized from methylene chloride/hexane to give the title compound as a white solid (10.5 g, 94%): m.p. 74.5°-77°; tlc, $R_f=0.45$, silica gel, ethyl acetate:hexane (1:1).

d. 2-Amino-3-methylbenzonitrile (Formula IV, A=formula Ia, Ra=methyl)

The benzonitrile prepared in Example 1c (4.5 g) was hydrogenated over 5% palladium on barium sulfate suspended in ethanol (105 ml) at atmospheric pressure. After filtering through diatomaceous earth to remove the catalyst, the solution was concentrated to leave a yellow solid (3.79 g). Purification by chromatographing the material over silica gel using ether:hexane (7:13) afforded the title product (2.53 g, 69%) as a cloudy, yellow oil: tlc, $R_f=0.44$, silica gel, ether:hexane (1:1).

2-(1-Propyl-2-oxo-3-pyrrolin-4-yl)amino-3-methylbenzonitrile (Formula II, A=formula Ia, X=N, Ra=methyl, Rb=propyl, n=1)

Freshly prepared 1-propyl-2,4-dioxopyrrolidine was prepared by heating together 3-carboethoxy1-propyl-2,4-dioxopyrrolidine (1.16 g) (U.S. Pat. No. 4,511,568, Example 52d describes the preparation of the methoxy compound: the ethoxy compound may be prepared in a similar manner), and acetonitrile (100 ml). After heating for 1.5 hours the volatiles were removed under aspirator vacuum and the residue consisting of crude 2,4-dioxopyrrolidine was taken up in toluene (4 ml). This solution was added dropwise to a refluxing mixture of 2-amino-3-methylbenzonitrile from Example 1d (0.48 g) and p-toluenesulfonic acid (36 mg) in toluene (10 ml). The refluxing mixture was surmounted with a Dean-Stark trap to collect water evolved in the reaction as the azeotrope with toluene. Following the addition of 2,4-dioxopyrrolidine (about 60 minutes), the mixture was heated for an additional 2 hours, then excess toluene was removed by distillation. After cooling to ambient temperature, the residue was partitioned between ethyl acetate and saturated aqueous $NaHCO_3$. After separation of the layers, the ethyl acetate layer was washed once with brine, dried ($MgSO_4$) and concentrated to leave an orange gum. Chromatographing the material over silica gel using ethyl acetate as the eluent afforded the desired product (0.70 g, 75%) as a white solid: tlc, $R_f=0.21$, silica gel, ethyl acetate.

EXAMPLE 2 a.
9-Amino-2,3-dihydro-5-butyl-2-propylpyrrolo[3,4-b]quinolin-1-one (Formula I, A=formula Ia, n=1, Ra=butyl Rb=propyl, Rc=H)

A mixture of the enamine (1.0 g) described in Example 2g and zinc bromide (0.16 g, which had been dried under high vacuum at 180° for 1 hour and cooled to ambient temperature) in methylene chloride (5.0 ml) maintained under an argon atmosphere was cooled in an ice bath. To this was added dropwise a methylene chloride solution (about 10 ml) of freshly prepared dipropylzinc (about 0.8 g). Following the addition, the reaction mixture was warmed to ambient temperature and stirred for 1 hour. The mixture was then heated to reflux with stirring for 24 hours. After cooling to ambient temperature the mixture was quenched by pouring it slowly into excess cold aqueous saturated $NH_4Cl$. After stirring for 10 minutes, ethyl acetate was added and the layers separated. The aqueous phase was extracted with additional ethyl acetate and the combined organic layer was washed with brine, dried over $MgSO_4$ and concentrated. The crude product was purified by column chromatography over silica gel using ethyl acetate:hexane (2:3) as the eluent. The isolated product was then recrystallized from tert-butylmethyl ether to afford the title compound (0.42 g, 41%) as an off-white crystalline solid; m.p. 126°-126.5°; tlc, $R_f=0.40$, silica gel, ethyl acetate:hexane (1:1).

Analysis calculated for $C_{18}H_{24}N_3O$: C, 72.69; H, 7.79; N, 14.13. Found: C, 72.74; H, 7.74; N, 14.13.

b. 3-[Z-(Dimethylamino)ethenyl-Z-nitrobenzonitrile

A mixture of 3-methyl-2-nitrobenzonitrile from Example 1c (5.72 g) and tert-butoxy-bis(dimethylamino)methane (9.5 ml) in dimethylformamide (30 ml) was heated to 90° with stirring for 1.5 hours. After cooling to ambient temperature the mixture was partitioned between ethyl acetate and water. The layers were separated with the aqueous phase further extracted using two portions of ethyl acetate. The combined ethyl acetate layer was washed with water then brine. The solution was dried over $MgSO_4$ and filtered through a small pad of silica gel. After concentrating the material a very dark brown solid was obtained. Recrystallization from ethyl acetate/hexane gave the title product (6.99 g, 91%) as dark brown crystals.

c. 3-Cyano-2-nitrobenzaldehyde

To a solution of the enamine (1.55 g) prepared in Example 2b in tetrahydrofuran:water (35 ml: 7 ml) was added osmium tetroxide (about 30 mg). After stirring for 10 minutes, $NaIO_4$ (1.0 g) was added all at once maintaining the reaction temperature at less than 28° by a cool water bath. Over the next 30 minutes, four portions of $NaIO_4$ (0.5 g per portion) were added about 6-8 minutes apart. A few minutes after the last portion of $NaIO_4$ was added, a final portion (0.21 g) was added for a total of 3.21 g of $NaIO_4$. The reaction was maintained at a temperature of less than 30° throughout the addition. After stirring for 1.5 hours, ethyl acetate and additional water were added. The layers were separated and the aqueous layer was extracted with additional ethyl acetate. The combined ethyl acetate layer was washed with brine, dried over $Na_2SO_4$ and concentrated. Chromatographic isolation over silica gel using ethyl acetate:hexane (2:3) as the eluent afforded the aldehyde (1.01 g, 80%) as a yellow solid: m.p. 109°-111°; tlc, $R_f=0.34$, silica gel, ethyl acetate:hexane (1:1).

d. 3-(Hydroxymethyl)-2-nitrobenzonitrile

To a solution of $NaBH_4$ (0.2 g) in ethanol (10 ml) at ice bath temperature was added a solution of 3-cyano-2-nitrobenzaldehyde from Example 2c (0.93 g) in ethanol:tetrahydrofuran (15 ml:15 ml). After the addition was completed, the solution was warmed to ambient temperature and stirred for 30 minutes. The volatiles were removed under aspirator vacuum and the residue suspended in water. Dilute (1% aqueous) hydrochloric acid was added slowly until gas evolution had ceased. Ethyl acetate was then added followed by saturation of the aqueous layer with $K_2CO_3$. The layers were separated and the ethyl acetate layer was washed with brine, dried ($Na_2SO_4$) and concentrated to leave the title product (0.85 g, 90%) as a yellow solid: tlc, $R_f=0.25$, silica gel, ethyl acetate:hexane (1:1).

e. 2-Amino-3-(hydroxymethyl)benzonitrile (Formula IV, A=formula Ia, Ra=hydroxymethyl)

To a suspension of zinc dust (1.84 g) in tetrahydrofuran (8.0 ml) stirred mechanically at 0° under an argon atmosphere was slowly added titanium (III) chloride (10 ml of a 20% (w/w) solution in water). The mixture was stirred vigorously for 30 minutes at ice bath temperature. A solution of 3-(hydroxymethyl)-2-nitrobenzonitrile from Example 2d (1.0 g) in tetrahydrofuran (4.0 ml) was then added over a 2-3 minutes period to the zinc-titanium (III) chloride mixture. After stirring for 15 minutes, aqueous sodium hydroxide (20%) was added to bring the pH of the mixture to about 7. Addition of more water and some ethyl acetate was necessary to allow efficient stirring. The mixture was filtered through a pad of diatomaceous earth. The pad of diatomaceous earth was mixed with fresh ethyl acetate after filtration and the suspension was re-filtered through fresh diatomaceous earth. The combined filtrates were separated and the separated aqueous phase extracted with fresh ethyl acetate. The combined ethyl acetate layer was washed with brine, dried ($Na_2SO_4$) and concentrated. The crude product was purified by chromatographing it over silica gel using ethyl acetate:hexane (1:1) as the eluent. The title product was obtained (0.71 g, 85%) as a light yellow solid; m.p. 117°-119.5°; tlc, $R_f=0.37$, silica gel, ethyl acetate:hexane (1:1).

f. 2-(1-Propyl-2-oxo-3-pyrrolin-4-yl)amino-3-(hydroxymethyl)benzonitrile (Formula IIa, A=formula Ia, X=N, n=1, Ra=hydroxymethyl, Rb=propyl)

Using the procedure described in Example 1e, freshly prepared 1-propyl-2,4-dioxopyrrolidine was made from 3-carboethoxy-1-propyl-2,4-dioxopyrrolidine (21.3 g) in acetonitrile (3500 ml). A mixture of the 1-propyl-2,4-dioxopyrrolidine, 2-amino-3-(hydroxymethyl)benzonitrile from Example 2e (9.87 g), and p-toluenesulfonic acid (0.64 g) in toluene:methylene chloride (50 ml:50 ml) was heated to gentle reflux. The reaction mixture was surmounted with a Dean-Stark trap to remove water removed as an azeotrope with methylene chloride and toluene. Heating was continued until about 50 ml of solvent had been collected. An additional portion of methylene chloride (75 ml) was added and 50 ml was additionally collected. The mixture was cooled to ambient temperature and partitioned between ethyl acetate and saturated aqueous $NaHCO_3$. The layers were separated and the aqueous phase extracted with additional ethyl acetate. The combined organic layer was washed with water then brine. After drying ($MgSO_4$) and concentrating, the crude product was purified by chromatographing it over silica gel using ethyl acetate:hexane (2:3) as the eluent. The enamine (17.4 g, 96%) was obtained as a viscous liquid which slowly solidified upon standing: tlc, $R_f=0.17$, silica gel, ethyl acetate:hexane (1:1).

g. Z-(1-Propyl-Z-oxo-3-pyrrolin-4-yl)amino-3-(chloromethyl)benzonitrile (Formula IIa, A'=formula Ia, X=N, n=1, Ra=—$CH_2Cl$, Rb=propyl)

The enamine prepared in Example 2f (6.31 g) was mixed with triphenylphosphine (6.69 g) and carbon tetrachloride (ZZ.5 ml) in methylene chloride (50 ml). After stirring overnight (about 15 hours) an additional portion of triphenylphosphine (1.83 g) was added and the mixture stirred for an additional 4 hours. The volatiles were removed and the residue partitioned between ethyl acetate and water. The layers were separated and the aqueous phase was extracted using additional ethyl acetate. The combined organic layer was washed with brine, dried and concentrated. The residual oil was dissolved in methylene chloride:hexane (1:1, 60 ml) and scratching begun until induction of crystallization. After a few hours the desired product was filtered off and the product was washed with methylene chloride:hexane (1:1). The filtrate was concentrated and the resulting solid residue (mostly triphenylphosphine oxide) was recrystallized from tert-butylmethyl ether. After filtering off the triphenylphosphine oxide the filtrate was concentrated, then recrystallized from methylene chloride:hexane (1:1) to obtain an additional crop of the title compound. The title product was obtained (4.21 g, 62% total yield) as a light yellow crystalline solid; m.p. 170°–172.5°; tlc, $R_f$=0.12, silica gel, ether.

EXAMPLES 3–6

The process described in Example 2a was repeated to obtain compounds of formula I, wherein A=formula Ia, X=N, n=1, Rb=propyl, Rc=H and wherein Ra was varied as listed in Table I. To obtain compounds of formula I as shown in Table I the following diorganozinc reagents were used in place of dipropyl zinc: Example 3: diethylzinc: Example 4: bis(2-methylpropyl)zinc: Example 5: bis(2-propyl)zinc: and Example 6: diphenylzinc.

the cadmium salts. The layers were separated with the aqueous phase extracted with additional ethyl acetate. The combined organic layer was washed once with saturated aqueous. NaHCO$_3$, then brine, followed by drying over Nahd 2SO$_4$. Concentration of the material followed by chromatographic purification over silica gel using ethyl acetate:hexane (1:1) as the eluent afforded a yellow-pink solid. Recrystallization from tert-butylmethyl ether/hexane gave the title quinoline (0.69 g, 57%) as a light yellow solid: m.p. 202°–203.5°; tlc, $R_f$=0.40, silica gel, ethyl acetate:hexane (1:1).

Analysis calculated for $C_{19}H_{19}N_3OS$: C, 67.63; H, 5.68: N, 12.45. Found: C, 67.29; H, 5.41: N, 12.36.

b.
2-(1-Propyl-2-oxo-3-pyrrolin-4-yl)amino-3-(2-thienyl)-methylbenzonitrile (Formula II, A=formula Ia, X=N, n=1, Ra=2-thienylmethyl Rb=propyl)

To a suspension of the enamine from Example 2g

TABLE I

| Example | Ra | Yield | m.p. | Elemental Analysis |
|---------|-----|-------|------|--------------------|
| 3 | propyl | 66% | 159–160°** | Calculated for $C_{17}H_{21}N_3O$: C, 72.06; H, 7.47: N, 14.83 Found: C, 72.08; H, 7.50: N, 14.08 |
| 4 | 3-methylbutyl | 44% | 125–128°** | Calculated for $C_{19}H_{25}N_3O$: C, 73.29; H, 8.09: N, 13.49 Found: C, 72.96; H, 8.06: N, 13.34 |
| 5 | 2-methylpropyl | 35% | 154–155°* | Calculated for $C_{18}H_{23}N_3O$: C, 72.70; H, 7.79: N, 14.13 Found: C, 72.70; H, 7.68: N, 14.10 |
| 6 | benzyl | 23% | 219–220.5°** | Calculated for $C_{21}N_{21}N_3O$: C, 76.11; H, 6.39: N, 12.68 Found: C, 75.81: H, 6.64: N, 12.22 |

*Recrystallization solvent was t-butylmethyl ether/hexane.
**Recrystallization solvent was t-butylmethyl ether.

EXAMPLE 7 a.
9-Amino-2,3-dihydro-5-(2-thienylmethyl)-2-propylpyrrolo[3,4-b]quinolin-1-one (Formula I, A=formula Ia, X=N, n=1, Ra=2-thienylmethyl, Rb=propyl, Rc=H)

Sodium hydride (0.17 g, 55% in oil) was washed under argon with freshly distilled tetrahydrofuran followed by resuspension in tetrahydrofuran (2.0 ml) and cooling in an ice bath. A solution of the enamine (1.20 g) prepared in Example 7b in tetrahydrofuran (5 ml) was then added dropwise to the rapidly stirred sodium hydride suspension. Following the addition the mixture was warmed slowly to ambient temperature with stirring until gas evolution ceased (about 30 minutes). To the stirred mixture was added all at once dry cadmium chloride (0.81 g) followed by slow warming to vigorous reflux. Once the mixture was refluxing, toluene (5.0 ml) was added and heating continued until the heating bath (silicone oil) temperature reached 110°. After 2 hours the mixture was cooled to ambient temperature and quenched with water. Ethyl acetate was added followed by a few ml of saturated aqueous ethylenediaminetetracetic acid disodium salt to remove (1.80 g) at 0° and dry zinc bromide (0.28 g) in methylene chloride (15 ml) was added dropwise bis(2-thienyl)zinc (about 3.5 g) in methylene chloride (10 ml). After stirring 1 hour at 0° and 2 hours at ambient temperature, the mixture was quenched by pouring it slowly into excess cold aqueous saturated NH$_4$Cl. After stirring several minutes ethyl acetate was added, the layers were separated and the aqueous layer was extracted with additional ethyl acetate. The combined organic layer was washed with brine, dried over Na$_2$SO$_4$ and concentrated. Purification by column chromatography over silica gel using ethyl acetate: hexane (1:1) as the eluent afforded the title compound as a yellow gum, (1.22 g, 58%): tlc, $R_f$=0.36, silica gel, ethyl acetate:hexane (3:1).

EXAMPLES 8–9

The process described in Example 7 was repeated for the synthesis of compounds of the formula II where A=formula Ia, Rb=propyl, Rc=H, X=N, n=1, and Ra=cyclopentylmethyl (Example 8) or cyclopropylmethyl (Example 9) by substituting the diorganozinc reagents dicyclopentylzinc and dicyclopropylzinc, respectively, for the bis(2-thienyl)zinc in Example 7b. The results of these Examples are included in Table II.

TABLE II

| Example | Ra | Enamine Yield | Quinoline Yield | m.p. | Elemental Analysis |
|---------|-----|---------------|-----------------|------|--------------------|
| 8 | cyclopentyl-methyl | 99% | 48% | 160–160.5° | Calculated for $C_{20}H_{25}N_3O$: C, 74.27; H, 7.79: N, 12.99 Found: C, 73.88; H, 7.75; N, 12.93 |
| 9* | cyclopropyl- | 60% | 77% | 157.5–158° | Calculated for $C_{18}H_{21}N_3O$: |

TABLE II-continued

| Example | Ra | Enamine Yield | Quinoline Yield | m.p. | Elemental Analysis |
|---------|-----|---------------|-----------------|------|---------------------|
|         | methyl |           |                 |      | C, 73.19; H, 7.17; N, 14.23 Found: C, 73.24; H, 7.15; N, 14.16 |

*The dicyclopropylzinc used (instead of bis(2-thienyl)zinc) was prepared by a method described in Method. der Organischen Chemie, supra, at page 598.

EXAMPLE 10 a. 9-Amino-2,3-dihydro-5-pentyl-2-propylpyrrolo[3,4-b]quinolin-1-one (Formula I, A=formula Ia, X=N, n=1, Ra=pentyl, Rb=propyl, Rc=H)

The procedure described in Example 7a was followed except for the following changes or substitutions: the enamine from Example 10f (1.10 g) was used instead of the enamine of Example 7b; NaH (0.79 g, 55% in oil instead of 0.17 g), tetrahydrofuran (5.0 ml instead of 2.0 ml), cadmium chloride (0.79 g instead 0.81 g) and toluene (5.0 ml instead of the amount indicated in Example 7a). After completion of the reaction and isolation of the crude product as described in Example 7a, the product was purified by column chromatography over silica gel using ethyl acetate:hexane (3:7) as the eluent. Recrystallization of the product afforded the title compound as a white solid (0.73 g, 66%): m.p. 140.5°-142°; tlc, $R_f=0.38$, silica gel, ethyl acetate:hexane (1:1).

Analysis calculated for $C_{19}H_{25}N_3O$ C, 73.29; H, 8.09; N, 13.49. Found: C, 73.37; H, 8.06; N, 13.64.

b. N-(Isonitrosoacetyl)-2-pentylaniline

To a warm (about 40°-45°) solution of chloral hydrate (10.1 g) and sodium sulfate decahydrate (108 g) in 400 ml of water was added a solution of 2-pentylaniline hydrochloride (10.3 g) in 400 ml of water. A solution of hydroxylamine hydrochloride (11.7 g) in water (65 ml) was next added and the mixture heated rapidly until an internal temperature of about 103-104° was achieved. The mixture was stirred for 15 minutes at this temperature followed by cooling in an ice bath and adding ethyl acetate. The layers were separated with the aqueous phase further extracted with ethyl acetate. The combined organic phase was washed with brine, dried over $Na_2SO_4$ and concentrated. Purification by column chromatography over silica gel using ethyl acetate:hexane (1:4) afforded the title product as a brown oil (9.1 g, 75%): tlc, $R_f=0.28$, silica gel, ethyl acetate:hexane (1:3).

c. 7-Pentylisatin

To warm (about 50°) concentrated sulfuric acid (30 ml) was added in several portions the product described in Example 10b (9.1 g). The mixture was rapidly warmed to 80° then stirred for 3-4 minutes. After cooling, the mixture was poured with stirring onto ice/water (400 ml). The crude orange solid was extracted with ethyl acetate. The ethyl acetate layer was washed with brine, dried over $Na_2SO_4$ and then poured through a small pad of silica gel. Recrystallization of the crude product from tert-butylmethyl ether/hexane gave the title product as an orange solid (5.51 g, 66%): m.p. 119°-121°; tlc, $R_f=0.31$, silica gel, ethyl acetate:hexane (1:3).

d. 7-Pentylisatin-3-oxime

A suspension of the isatin described in Example 10c (5.51 g) in ethanol (ZO ml) was warmed slightly followed by addition of hydroxylamine hydrochloride (2.47 g) dissolved in water (10 ml). The mixture was warmed to about 80° with stirring for 10 minutes, followed by cooling to ambient temperature and stirring for 30 minutes. The precipitated yellow solid was filtered off, washed with water and dried to afford the title product (4.50 g, 76%) as a fluffy yellow powder: tlc, $R_f=0.16$, silica gel, ethyl acetate:hexane (2:3).

e. 2-Amino-3-pentylbenzonitrile (Formula IV, Ra=pentyl, A=formula Ia)

Sodium metal (1.11 g) was reacted with methanol (10 ml). The excess methanol was removed under high vacuum while heating the residue (sodium methoxide) to 140°. The residue was suspended in diethylene glycol (10 ml) followed by addition of the isatin oxime (4.50 g) described in Example 10d. The mixture was heated rapidly to 195° ($\pm 10°$) for 30 minutes. After cooling to ambient temperature, the mixture was partitioned between ethyl acetate and water. The aqueous phase was separated and extracted three times with ethyl acetate:ether (1:1). The combined organic layer was dried ($MgSO_4$) and concentrated to a purple oil. Purification by column chromatography over silica gel using ethyl acetate: hexane (1:9) as the eluent gave the desired compound (2.17 g, 59%) as a brown oil: tlc, $R_f=0.60$, silica gel, ethyl acetate:hexane (1:1).

f. 2-(1-Propyl-2-oxo-3-pyrrolin-4-yl)amino-3-pentylbenzonitrile (Formula II, A=formula Ia, X=N, n=1, Ra=pentyl, Rb=propyl)

Freshly prepared 1-propyl-2,4-dioxopyrrolidine generated as described in Example 1e from 3-carboethoxy-1-propyl-2,4-dioxopyrrolidine (1.88 g) in acetonitrile (400 ml) was taken up in toluene (3 ml). This solution was added dropwise to a refluxing solution of 2-amino-3-pentylbenzonitrile (0.83 g, Example 10e) and ..p-toluene-sulfonic acid (catalytic) in toluene (5 ml). The toluene/water azeotrope evolved was removed by a Dean-Stark trap. Following the addition of the 1-propyl-2,4-dioxopyrrolidine (about 45 minutes) the mixture was heated at reflux for 3 hours. The excess toluene was distilled off and the residue cooled to ambient temperature. The residue was partitioned between ethyl acetate and saturated aqueous $NaHCO_3$ and the layers were separated. The aqueous phase was extracted once with ethyl acetate, then the combined ethyl acetate layer was washed with brine, dried over $Na_2SO_4$ and concentrated to a brown oil. Chromatographic isolation of the material over silica gel using ethyl acetate:hexane (3:2) as the eluent afforded the title product as a thick gum (1.12 g, 82%) which slowly solidified upon standing: tlc, $R_f=0.43$, silica gel, ethyl acetate.

EXAMPLE 11 a.

9-Amino-5-methyl-2-(2-propenyl)-2,3-dihydrocyclopenta[b]quinolin-1-one (Formula I, A = formula Ia, X = >C-H, n = 1, Ra = methyl, Rb = Z-propenyl, Rc = H)

The enamine described in Example 11b (1.53 g) was mixed under nitrogen with copper(1) acetate (1.48 g) in dimethylformamide (17 ml). The mixture was lowered into a pre-heated oil bath at 125° and stirred for 3.5 hours. After cooling, the volatiles were removed in vacuo and the residue partitioned between methylene chloride and aqueous NH$_4$OH. The layers were separated and the aqueous phase was further extracted with methylene chloride. The combined methylene chloride layer was filtered to remove some suspended particulate matter. The organic layer was dried over MgSO$_4$ and concentrated to leave 1.04 g of a brown solid. Chromatography over silica gel using methanol:methylene chloride (3:97) as the eluent gave 0.34 g (22%) of the title compound: m.p. 188.5°–190°; tlc, R$_f$=0.26, silica gel, methanol:methylene chloride (3:97).

Analysis calculated for $C_{16}H_{15}N_2O$: C, 76.16: H, 6.39: N, 11.10. Found: C, 75.91: H, 6.41: N, 11.00.

b.

2-[1-Oxo-5-(2-propenyl)-2-cyclopenten-3-yl]amino-3-methylbenzonitrile (Formula II, A = formula Ia, X = >C-H, n = 1, Ra = methyl, Rb = 2-propenyl)

The product described in Example 1d (1.55 g) was refluxed together with 4-(2-propenyl)-1,3-cyclopentanedione (1.7 g) (prepared as described in U.S. Pat. No. 4,546,104 and p-toluenesulfonic acid (0.25 g) in toluene (36.5 ml). The water evolved was removed as the azeotrope with toluene in a Dean-Stark trap. After heating for 6 hours the volatiles were removed in vacuo and the crude residue chromatographed over silica gel using methanol:methylene chloride (9:191). There was obtained a dark amber powder (1.53 g, 52%) as the title product: tlc, R$_f$=0.26, silica gel, methanol:chloroform (1:24).

EXAMPLE 12 a.

9-Amino-5-pentyl-2-(2-propenyl)-2,3-dihydrocyclopenta[b]quinolin-1-one (Formula I, A = formula Ia, X = >C-H, n = 1, Ra = pentyl, Rb = Z-propenyl, Rc = H)

A procedure similar to that described in Example 7a was followed, however, the following changes and substitutions were made: the enamine described in Example 12b (1.21 g), 0.186 g of sodium hydride, 0.86 g of anhydrous cadmium chloride in tetrahydrofuran (4 ml instead of 2.0 ml) and toluene (5.0 ml). After work-up and isolation of the crude product as described in Example 7a, the material was chromatographed over silica gel using ethyl acetate:hexane (1:1) as the eluent. Recrystallization from tert-butylmethyl ether/hexane gave the title product (0.71 g, 59%) as a light yellow solid; m.p. 90°–91.5°; 91.5°; tlc, R$_f$=0.58, silica gel, ethyl acetate:hexane (1:1).

Analysis calculated for $C_{20}H_{24}N_2O$: C, 77.89; H, 7.84; N, 9.08. Found: C, 77.78: H, 7.95: N, 8.95.

b.

2-[1-Oxo-5-(2-propenyl)-2-cyclopenten-3-yl]amino3-pentylbenzonitrile (Formula II, A = formula Ia, X = >C-H, n = 1, Ra = pentyl, Rb = 2-propenyl)

A procedure similar to that described in Example 11b was followed using the following changes and substitutions: 2-amino-3-pentylbenzonitrile (1.51 g) from Example 10e instead of the nitrile from Example 1d, and 4-(2-propenyl)-1,3-cyclopentanedione (1.30 g instead of the amount indicated in Example 11b) in toluene (10 ml instead of the amount indicated in Example 11b). Following a heating interval of 5.5 hours, excess toluene was distilled off and the residue cooled to ambient temperature. Partitioning of the residue between saturated aqueous NaHCO$_3$ and ethyl acetate was followed by separation of the layers and washing of the ethyl acetate layer with brine. After drying and concentrating the material, the crude product was chromatographed over silica gel using ethyl acetate:hexane (1:1) as the eluent. There was obtained the title product (1.21 g, 49%) as a yellow gum: tlc, R$_f$=0.23, silica gel, ethyl acetate: hexane (1:1).

EXAMPLE 13 a.

8-Amino-3-pentyl-6-propyl-5,6-dihydrothieno[3,4-e]pyrrolo[3,4-b]pyridin-7(1H)-one (Formula I, A = formula Ib, X = N, Y = S, n = 1, Ra = pentyl, Rb = propyl, Rc = H)

The product described in Example 13d (0.73 g) was added to a stainless steel bomb to which was also added ethanol (15 ml) which had been pre-saturated with gaseous ammonia at 0°. The bomb was sealed then heated to 100° overnight (about 15 hours). After cooling and concentrating the material, the resulting dark solid was purified by column chromatography over silica gel using ethyl acetate:hexane (1:1) as the eluent. The chromatographed material was recrystallized from ethyl acetate/ether to give a yellow solid (0.50 g, 72%) as the title product: m.p. 167°–169°; tlc, R$_f$=0.20, silica gel. ethyl acetate:hexane (1:1).

Analysis calculated for $C_{17}H_{23}N_3OS$: C 64.32: H, 7.30: N, 13.24. Found: C, 64.15: H, 7.34: N, 13.10.

b.

3-(1-Propyl-2-oxo-3-pyrrolin-4-yl)amino-2-pentyl-4-carbomethoxythiophene

Freshly prepared 1-propyl-Z,4-dioxopyrrolidine was prepared as described in Example 1e from 3-carboethoxy-1-propyl-2,4-dioxopyrrolidine (3.55 g) in acetonitrile (100 ml). The 1-propyl-2,4-dioxopyrrolidine was mixed with methyl 3-amino-2-pentylthiophene- 4-carboxylate (2.70 g) in toluene (65 ml). The mixture was refluxed for 2 hours with removal of the water/toluene azeotrope using a Dean-Stark trap. After distilling off the excess toluene, the residue was taken up in ethyl acetate, washed sequentially with saturated aqueous Na$_2$CO$_3$ and brine, then dried (Na$_2$SO$_4$) and concentrated. Chromatographic purification over silica gel afforded the title product (3.92 g, 94%) as a yellow oil; tlc, R$_f$=0.12, silica gel, ethyl acetate:hexane (1:1). c. 5,6-Dihydro-8-hydroxy-3-pentyl-6-propyl-pyrrolo[3,4-b]thieno[3,4-e]pyridin-7(1H)-one (Formula VII, n = 1, X = N, Ra = pentyl, Rb = propyl, W = OH)

A solution of the enamine (1.70 g) described in Example 13b was added to a solution of freshly prepared sodium ethoxide in ethanol (0.11 g of sodium in 5.0 ml ethanol). An additional 10 ml of ethanol was required to assist stirring, then the reaction was stirred for 16 hours at ambient temperature. The mixture was poured into water (25 ml) and the resulting precipitate collected to afford the title product (1.2 g, 78%) as a yellow solid: m.p. greater than 285°: tlc, $R_f=0.05$, silica gel, methanol:chloroform (1:19).

d.
8-Chloro-3-pentyl-6-propyl-5,6-dihydrothieno[3,4-e]pyrrolo[3,4-b]pyridin-7(1H)-one (Formula III, n=1, X=N, Ra=pentyl, Rb=propyl, Z=Cl)

The product described in Example 13c (0.94 g) was suspended in thionyl chloride (25 ml) followed by the addition of a few drops of dimethylformamide. After 30 minutes at ambient temperature excess thionyl chloride was removed under aspirator vacuum. Ether was added to the residue to give a precipitate. Filtration afforded the title product (0.73 g, 74%) as an orange powder: tlc, $R_f=0.88$, silica gel, methanol: chloroform (1:19).

EXAMPLES 14-15

The process described in Example 13d was repeated using butyl and propyl-substituted thiophenes made according to the method described in U.S. Pat. No. 4,317,915 to prepare compounds of formula IV where Ra=butyl and propyl and A=formula Ib. These butyl- and propyl-substituted thiophenes were used for Examples 14 and 15 respectively. Table III lists compounds of formula I with A=formula Ib, X=N, n=1, Rb=propyl, and Rc=H, and where Ra has a value as shown in the table.

TABLE III

| Example | Ra | Yield* | m.p. | Elemental Analysis |
|---|---|---|---|---|
| 14 | butyl | 22% | 184–185°** | Calculated for $C_{16}H_{21}N_3OS$ C, 63.33; H, 6.98; N, 13.85 Found: C, 63.37; H, 7.02; N, 13.68 |
| 15 | propyl | 26% | 200–202°*** | Calculated for $C_{15}H_{19}N_3OS$ C, 62.25; H, 6.62; N, 14.52 Found: C, 61.66; H, 6.58; N, 14.28 |

*Yield is for last step.
**Recrystallized from t-butylmethyl ether/hexane/ethyl acetate.
***Recrystallized from ethyl acetate/hexane.

EXAMPLE 16 a.
8-Amino-5,6-dihydro-3-pentyl-6-propyldipyrrolo[3,2-b:3,4-e]pyridin-7(1H)-one (Formula I, A=formula Ic, X=N, Y= >N-Rd, n=1, Ra=pentyl, Rb=propyl, Rc=H, Rd=H)

A procedure similar to that described in Example 7a was followed using the enamine prepared in Example 16e (1.65 g) instead of the enamine from Example 7b, sodium hydride (0.25 g, 55% in oil instead of .17 g) and cadmium chloride (1.05 g) in toluene (Z0 ml) with the same amount of tetrahydrofuran (2 ml) as used in Example 7a. A small amount of dimethylformamide was also present to help solubilize the enamine at the beginning of the reaction. Following the heating interval (1.5 hours at 110°) the mixture was cooled to ambient temperature and concentrated in vacuo. The residue was partitioned using water and ethyl acetate:tetrahydrofuran (2:1) with a little ethylenediaminetetraacetic acid (EDTA) added. The layers were separated and the aqueous phase was extracted with additional ethyl acetate. The combined organic layer was washed with brine, dried (MgSO$_4$) and concentrated. The crude product was chromatographed over silica gel using methanol:methylene chloride (1:19) as the eluent. The resulting solid was recrystallized from tetrahydrofuran/ethyl acetate/methanol to leave the title product as a white solid (1.01 g, 61%): m.p. greater than 225° tlc, $R_f=0.13$, silica gel, methanol:chloroform (1:19).

Analysis calculated for $C_{17}H_{24}N_4O$: C, 67.96; H, 8.05; N, 18.65. Found: C, 67.60; H, 7.92; N, 18.18.

b. 2-Formylheptanonitrile

A solution of potassium tert-butoxide (18.9 g) in a mixed solvent system of tetrahydrofuran (150 ml) and toluene (100 ml) was heated to 75°. A solution of heptanonitrile (11.2 g) and ethyl formate (24 ml) in toluene (50 ml) was then added dropwise to the warm tert-butoxide solution. The reaction was stirred for 5 hours at 75° then cooled with an ice bath. Ether was added to the mixture and then water. The layers were separated. The aqueous phase was washed once with ether then acidified to a pH of about 3 with aqueous hydrochloric acid (6N). The aqueous phase was saturated with sodium chloride then extracted twice with ether. The combined ether extracts were washed with brine, dried (MgSO$_4$) and concentrated to leave the title product as a yellow oil (10.7 g, 77%).

c. 2-[(Cyanomethyl)aminomethylene]heptanonitrile

2-Formylheptanonitrile (10.7 g), sodium acetate (7.9 g) and aminoacetonitrile hydrochloride (8.9 g) were mixed together in 200 ml of methanol: water (8:2). After stirring for 2 hours at ambient temperature the methanol was removed under aspirator vacuum and the residue partitioned between ethyl acetate and water. The layers were separated and the ethyl acetate layer was washed with brine, dried (Na$_2$SO$_4$) and concentrated to leave a yellow oil. Chromatographic purification of the material over silica gel using ethyl acetate/hexane as the eluent afforded a light yellow solid as a mixture of isomers (11.6 g, 85%): tlc, $R_f=0.37$ and 0.50 silica gel, ethyl acetate:hexane (1:1).

d. 3-Amino-2-cyano-4-pentylpyrrole (Formula IV, A=formula Ic, Y= >N-Rd, Ra=pentyl, Rd=H)

To a solution at 0° of the product described in Example 16c (11.1 g) and triethylamine (10.4 ml) in methylene chloride (100 ml) was added dropwise ethyl chloroformate (6.90 ml). The resulting dark mixture was stirred for one hour at 0° followed by warming to ambient temperature and adding 1,8-diazabicyclo[5.4.0]undec-7-ene (11.2 ml). The mixture was warmed to reflux and stirred for 6 hours. The mixture was then cooled to ambient temperature and stirred overnight (about 16 hours). The mixture was partitioned between ether and water and the layers separated. The aqueous phase was further extracted with ethyl acetate and the combined organic layer was washed with brine, dried (MgSO$_4$)

and concentrated to leave a dark oil. This oil was stirred with anhydrous powdered Na$_2$CO$_3$ (1 g) in methanol at ambient temperature for one hour. The volatiles were removed and the residue partitioned between ether and water. The layers were separated and the aqueous phase extracted three times with ether. The combined ether layer was washed with brine, dried (MgSO$_4$) and concentrated. The crude product was chromatographed over silica gel using ethyl acetate: hexane (1:4) as the eluent. The resulting orange solid was recrystallized from toluene/hexane to give the title product as an off-white powder (6.05 g, 54%): m.p. 49°–50.5°; tlc, R$_f$=0.26, silica gel, ethyl acetate:hexane (1:3).

e.

3-(1-Propyl-2-oxo-3-pyrrolin-4-yl)amino-4-pentyl2-cyanopyrrole (Formula II, A=formula Ic, X=N, Y= >N-Rd, n=1, Ra=pentyl, Rb=propyl, Rd=H)

Fresh 1-propyl-2,4-dioxopyrrolidine was prepared as described in Example 1e from 3-carboethoxy-1propyl-2,4-dioxopyrrolidine (1.91 g) in acetonitrile (400 ml). The 1-propyl-2,4-dioxopyrrolidine was then condensed with 3-amino-2-cyano-4-pentylpyrrole (1.15 g) from Example 16d in toluene (20 ml) using a catalytic amount of p-toluenesulfonic acid. After heating at reflux for one hour using a Dean-Stark trap to remove the water evolved, the mixture was cooled to ambient temperature. The precipitated solid was filtered off and washed with ether to leave the title product as a white solid (1.78 g, 92%): tlc, R$_f$=0.08, silica gel, methanol:chloroform (1:19).

EXAMPLE 17 a.

8-Amino-3-pentyl-6-(2-propenyl)-4,5,6,7-tetrahydropyrrolo[3,2-b]quinolin-7-(1H)-one (Formula I, A=formula Ic, X= >C-H, Y= >N-Rd, n=2, Ra=pentyl, Rb=2-propenyl, Rc=H, Rd=H)

The enamine described in Example 17b (3.41 g) was cyclized according to the procedure described in Example 7a using sodium hydride (0.51 g, 55% in mineral oil instead of .17 g) and cadmium chloride (2.11 g instead of .81 g) in tetrahydrofuran (10.0 ml instead of 2.0 ml) and toluene (10.0 ml instead of the amount indicated in Example 7a). The reaction required 15 hours at 90°–95° to go to completion after which isolation of the crude product was accomplished as described in Example 7a. The crude material was chromatographed over silica gel using ethyl acetate: hexane (1:1) as the eluent to obtain the title product (2.66 g, 78%) as a white solid: m.p. decomposes at greater than 195° : tlc, R$_f$=0.29, silica gel, ethyl acetate:hexane (1:1) plus about 2% triethylamine.

Analysis calculated for
C$_{19}$H$_{25}$N$_3$O C, 73.19; H, 8.09; N, 13.49. Found: C, 72.58: H, 8.04; N, 13.21.

b.

3-[1-Oxo-5-(2-propenyl)-2-cyclohexen-3-yl]amino-4-pentyl-2-cyanopyrrole (Formula II, A=formula Ic, X= >C-H, Y=.N-Rd, n=2, Ra=pentyl, Rb=2-propenyl, Rc=H, Rd=H)

A mixture of 3-amino-2-cyano-4-pentylpyrrole (2.0 g) from Example 16d and 4-(2-propenyl)-1,3-cyclohexanedione (2.06 g, prepared as described in U.S. Pat. No. 4,546,104) was heated in toluene (25 ml) containing a catalytic amount of p-toluenesulfonic acid. The mixture was refluxed for 1.5 hours with removal of evolved water as the azeotrope with toluene using a Dean-Stark trap. After distilling off excess toluene and cooling to ambient temperature, the residue was partitioned between ethyl acetate and saturated aqueous NaHCO$_3$. The layers were separated. The ethyl acetate layer was washed with brine, dried (MgSO$_4$) and concentrated to a thick gum. Chromatographic purification of the material over silica gel using ethyl acetate:hexane as the eluent (2:3) afforded the title product (3.41 g, 97%): tlc, R$_f$=0.27, ethyl acetate: hexane (1:1).

EXAMPLE 18 a.

8-Amino-4,5-dihydro-3-pentyl-1H-6-(2-propenyl)pyrrolo[3,2-b][1,6]napthyridin-7(6H)-one (Formula I, A=formula Ic, X=N, Y=.N-Rd, n=2, Ra=pentyl, Rb=2-propenyl, Rd=H)

The procedure of Example 17a was followed using the enamine of Example 18e (0.71 g) instead of the enamine of Example 17b to obtain 0.30 g (46%) of the title compound as a yellow solid. Addition to ethereal HCl gave the hydrochloride salt which was recrystallized from ethanol.

Analysis calculated for C$_{18}$H$_{24}$N$_4$O.HCl.½H$_2$O: C, 60.41; H, 7.32; N, 15.65. Found: C, 60.14: H, 7.96: N, 15.28.

b. 4-Ethoxy-1,2,5,6-tetrahydro-1H-2-pyridone

A solution of 2,4-dioxipiperidine (2.0 g) in ethanol (45 ml) was heated to reflux in the presence of a catalytic amount of p-toluenesulfonic acid. After 5 hours at reflux the ethanol was removed and the residue triturated with tetrahydrofuran to give the title product as a brown solid (2.48 g): tlc, R$_f$=0.33, silica gel, methanol:chloroform (1:19).

c.

4-Ethoxy-1-(2-propenyl)-1,2,5,6-tetrahydro-2-pyridone

To a suspension of sodium hydride (0.85 g, 55% in mineral oil, pre-washed with tetrahydrofuran) in tetrahydrofuran (30 ml) maintained at ice bath temperature was slowly added the product from Example 18b (2.48 g). After 20 minutes 1-bromo-2-propene (1.52 ml) was slowly added. The mixture was warmed to ambient temperature and stirred for 48 hours. The mixture was diluted with water then extracted with ethyl acetate. After drying (MgSO$_4$) and concentrating the material, the residue was chromatographed over silica gel using methanol:chloroform (1:19) as the eluent. There was obtained 1.0 g (31%) of product: tlc, R$_f$=0.62, silica gel, methanol:chloroform (1:19).

d. 1-(2-Propenyl)-2,4-dioxopiperidine (Formula V, X=N, n=2, Rb=2-propenyl)

A solution of the product described in Example 18c (1.5 g) in tetrahydrofuran (10 ml) and aqueous hydrochloric acid (10 ml of 10%) was stirred at ambient temperature for about 15 hours. Sodium chloride was then added to saturate the aqueous phase and the mixture was extracted with several portions of ethyl acetate. The combined extracts were dried (MgSO$_4$) and concentrated to leave the title product as a clear oil (1.0 g, 79%); tlc, R$_f$=about 0.05, silica gel, methanol:chloroform (1:19).

e.
3-[1-(2-Propenyl)-2,4-dioxopiperidyl]-amino-4-pentyl-2-cyanopyrrole (Formula II, A=formula Ic, X=N, Y=>N-Rd, n=2, Ra=pentyl, Rb=Z-propenyl, Rd=H)

The process described in Example 17b was repeated using 1-(2-propenyl)-Z,4-dioxopiperidine (1.0 g) and 3-amino-Z-cyano-4-pentylpyrrole (0.53 g) to give 0.71 g (76%) of the title enamine.

EXAMPLE 19 a.
4-Amino-6,7-dihydro-1-pentyl-6-propyldipyrrolo[2,3-b:3,4-e]pyridin-5(1H)-one (Formula I, A=formula Id, X=N, n=1, Ra=pentyl, Rb=propyl, Rc=H)

The enamine prepared in Example 19c (0.75 g) was cyclized according to the procedure of Example 7a using sodium hydride (0.12 g, 55% in mineral oil instead of .17 g) and cadmium chloride (0.55 g instead of .81 g) in tetrahydrofuran (2 ml, the same amount as in Example 7a) and toluene (2 ml instead of the amount indicated in Example 7a) to give, after isolation of the crude product as described in Example 7a, a brown solid. The crude product was chromatographed over silica gel using methanol:methylene chloride (4:1) as the eluent. The solid obtained was recrystallized from tert-butyl-methyl ether/hexane to give the title compound as a white solid (0.52 g, 69%): m.p. 138°-138.5°; tlc, $R_f$=0.30, silica gel, methanol: chloroform (1:19).

Analysis calculated for $C_{17}H_{24}N_4O$: C, 67.97: H, 8.05: N, 18.65. Found: C, 68.18: H, 8.36: N, 17.97.

b. 2-Amino-3-cyano-1-pentylpyrrole (Formula IV, A=formula Id, Ra=pentyl)

To a solution of 1-carboethoxy-2-amino-3-cyanopyrrole (1.55 g, prepared according to the procedure described in Chem. Pharm. Bull: Vol. 30, 2357-2363 (1982)) in dry methanol (15 ml) was added $K_2CO_3$ (0.60 g). After 30 minutes at ambient temperature the methanol was removed in vacuo and the dark residue was taken up in dimethylformamide (15 ml). This solution was added to a suspension of sodium hydride (0.45 g, 55% in mineral oil, pre-washed with dry tetrahydrofuran) at 0° in dimethylformamide (5 ml). The mixture was warmed to ambient temperature with stirring for 10 minutes followed by the addition of 1-bromopentane (1.61 ml). The reaction was stirred for 15 minutes then poured into water and extracted with ethyl acetate. The ethyl acetate extracts were washed with water and then brine. The material was dried (MgSO4) and concentrated. The residue was chromatographed over silica gel, eluting with methanol:methylene chloride (1:49) to give the title product as a light brown oil (0.66 g, 43%): tlc, $R_f$=0.46, silica gel, methanol:chloroform (1:49).

c.
2-(1-Propyl-2-oxo-3-pyrrolin-4-yl)amino-3-cyano-1-pentylpyrrole (Formula II, A=formula Id, X=N, n=1, Ra=pentyl, Rb=propyl)

Fresh 1-propyl-2,4-dioxopyrrolidine was prepared as described in Example 1e from 3-carboethoxy-1-propyl-2,4-dioxopyrrolidine (1.01 g) in acetonitrile (100 ml). A mixture of the 1-propyl-2,4-dioxopyrrolidine and 2-amino-3-cyano-1-pentylpyrrole (0.60 g) from Example 19b was heated in toluene (10 ml) along with a catalytic amount of p-toluenesulfonic acid. The mixture was refluxed for one hour with removal of the toluene/water azeotrope in a Dean-Stark trap. After concentrating the material, the residue was partitioned between ethyl acetate and water; the layers were separated and the ethyl acetate layer was dried over MgSO4. After filtration and concentration the residue was chromatographed over silica gel using methanol:methylene chloride (3:1) to give the title product as a purple solid (0.95 g, 94%): tlc, $R_f$=0.34, silica gel, methanol:methylene chloride (3:1).

EXAMPLE 20 a.
4-Amino-b,7-dihydro-1-butyl-6-propyldipyrrolo[2,3-b:3,4-e]pyridin-5(1H)-one (Formula I, A=formula Id, X=N, n=1, Ra=butyl, Rb=propyl, Rc=H)

The process of Example 19a was repeated using the enamine of Example 20c (1.05 g), sodium hydride (0.18 g, 55% in mineral oil), and cadmium chloride (0.18 g) instead of the amounts and enamine used in Example 19a. Cyclization of the enamine gave the title compound (0.73 g, 69%): m.p. 169°-171°; tlc, $R_f$=0.24, silica gel, ethyl acetate:hexane (1:1).

Analysis calculated for $C_{16}H_{22}N_4O$: C, 67.11; H, 7.74: N, 19.56. Found: C, 66.96: H, 8.00: N, 19.06.

b. 2-Amino-3-cyano-1-butylpyrrole (Formula IV, A=formula Id, Ra=butyl)

The process described in Example 19b was repeated using 1.45 g of the 1-carboethoxy-2-amino-3-cyanopyrrole and 1-iodobutane (1.01 ml) to prepare the title compound (0.77 g, 58%).

c.
2-(1-Propyl-2-oxo-3-pyrrolin-4-yl)amino-3-cyano-1-butylpyrrole (Formula II, A=formula Id, X=N, n=1, Ra=butyl, Rb=propyl)

The process of Example 19b was repeated using the butylpyrrole of Example 19b to make the title enamine compound (1.05 g, 78%).

EXAMPLES 21-25

The process in Example 7 was repeated for the synthesis of compounds of formula II where A=formula Ia, Rb=propyl, Rc=H, X=N, n=1 and Ra is selected from 2-methylbutyl (Example 21): cyclohexylmethyl (Example 22); 2,2-dimethylpropyl (Example 23): 2-phenylethyl (Example 24): and (3-thienyl)methyl (Example 25) by substituting the appropriate diorganozinc reagents for bis(2-thienyl)zinc in Example 7b. The resulting enamines were then cyclized according to the process described in Example 7a to afford compounds of the formula I as listed in Table IV.

TABLE IV

| Example | Ra | Enamine Yield | Quinoline Yield | Quinoline m.p. | Elemental Analysis for Quinoline |
|---|---|---|---|---|---|
| 21 | 2-methylbutyl | 95% | 58%* | 138-139.5° | Calculated for $C_{19}H_{25}N_3O$: C, 73.28; H, 8.04; |

TABLE IV-continued

| Example | Ra | Enamine Yield | Quinoline Yield | Quinoline m.p. | Elemental Analysis for Quinoline |
|---|---|---|---|---|---|
| 22 | cyclohexylmethyl | 83% | 57%** | 186.5-18-7.5° | N, 13.49<br>Found: C, 73.53; H, 7.70; N, 13.46<br>Calculated for $C_{21}H_{27}N_3O$: C, 74.74; H, 8.06; N, 12.45<br>Found: C, 74.58; H, 8.00; N, 12.30 |
| 23 | 2,2-dimethylpropyl | 89% | 52%* | 175-177° | Calculated for $C_{19}H_{25}N_3O$: C, 73.28; H, 8.09; N, 13.49<br>Found: C, 73.27; H, 8.10; N, 13.46 |
| 24 | 2-phenylethyl | 84% | 76%*** | 187-190° | Calculated for $C_{22}H_{23}N_3O$: C, 76.49; H, 12.16; N, 6.71<br>Found: C, 76.12; H, 12.05; N, 6.64 |
| 25 | 3-thienylmethyl | 78% | 39%*** | 210-211° | Calculated for $C_{19}H_{19}N_3O.S$: C, 67.63; H, 5.68 N, 12.45<br>Found: C, 66.86; H, 5.62; N, 12.22 |

*Recrystallized from tert-butylmethyl ether/hexane
**Recrystallized from tert-butylmethyl ether/ethyl acetate
***Recrystallized from ethyl acetate

EXAMPLE 26 a. 9-Amino-2-benzyl-2,3-dihydro-5-(2-methylpropyl) pyrrolo[3,4-b]quinolin-1-one (Formula I, A=formula Ia, X=N, n=1, Ra=2-methylpropyl, Rb=benzyl, Rc=H)

The enamine from Example 26f plus an additional sample prepared as described in Examples 26 b-f (1.15 g) were reacted with sodium hydride (0.172 g, 55% in oil) in tetrahydrofuran as described in Example 7a. After warming to ambient temperature the cadmium chloride (7.63 g) was added and the mixture heated to reflux. A few milliliters (ml) of toluene were added and the heating continued (bath temperature=100°) for 40 minutes. After cooling to ambient temperature, saturated aqueous disodium ethylenediaminetetraacetic acid was added and the product worked up as described in Example 7a. The crude product was purified by column chromatography using ethyl acetate:methylene chloride (1:4) as the eluent. Recrystallization of the product in ethyl acetate afforded the product as a white solid (1.11 g, 96%): m.p., 167°-170°; tlc, $R_f$=0.55, silica gel, ethyl acetate:hexane (1:1).

Analysis calculated for $C_{22}H_{23}N_3O$: C, 76.49; H, 6.71; N, 12.16. Found: C, 76.35; H, 6.68; N, 12.08.

b. Ethyl N-(ethoxycarbonylacetyl)-N-benzylglycinate

To a 0° C. solution of ethyl N-benzylglycinate (8 g) in tetrahydrofuran (4 ml) and diethyl ether (42 ml) was added simultaneously a solution of $K_2CO_3$ (5.72 g) in 20 ml of water and ethyl malonylchloride (6.54 g) in 20 ml of diethyl ether. Following the addition the mixture was stirred at 0° for 1 hour then warmed to ambient temperature with stirring for 2 hours. The layers were separated with the organic phase washed once with brine. After drying ($Na_2SO_4$) and concentrating, there was obtained 12.5 g (98.8%) of the product as a viscous oil.

1-Benzyl-3-carboethoxy-2,4-pyrrolidione

The product from Example 26b (2.0 g) was dissolved in 13 ml of toluene. This solution was added dropwise over a 2 hour period to 6.4 ml of a 1M solution of sodium chloride in ethanol maintained at ambient temperature. Following the addition, the mixture was heated to reflux for 4.5 hours then cooled to ambient temperature. Water (10 ml) was added and the layers separated. The organic phase was washed with water (4×30 ml) and the aqueous phases were combined. The aqueous layer was acidified by adding 6N HCl (aqueous) to bring the pH to approximately 1. The resulting white precipitate was extracted with 3×50 ml of methylene chloride. After drying over $Na_2SO_4$, the volatiles were removed to leave 1.37 g (81%) of the product as a white solid.

d. 2-(1-Benzyl-2-oxo-3-pyrrolin-4-yl)amino-3-(hydroxymethyl)benzonitrile (Formula II, A=formula Ia, X=N, n=1, Ra=$CH_2OH$, Rb=benzyl)

The product described in Example 26c (0.75 g) was decarboethoxylated by boiling in acetonitrile (100 ml) as described in Example 1e for 1-propyl-2,4-dioxopyrrolidine. The freshly prepared 1-benzyl-2,4-dioxopyrrolidine was reacted with 0.35 g of 2-amino-3-(hydroxymethyl)benzonitrile (Example 2e) according to the procedure described in Example 2f. Following isolation of the product as described in Example 2f there was obtained 0.8 g (quantitative) of a gummy oil: tlc, $R_f$=0.13; silica gel, ethyl acetate:hexane (3:2).

e. 2-(1-Benzyl-2-oxo-3-pyrrolin-4-yl)amino-3-(chloromethyl)benzonitrile (Formula IIa, A'=formula Ia, X=N, n=1, Ra=CH2Cl, Rb=benzyl)

The product obtained in Example 26d (0.8 g) was reacted with triphenylphosphine (0.72 g) and $CCl_4$ (2.41 ml) in 25 ml of methylene chloride according to the procedure of Example 2g. After 20 hours an additional portion of triphenylphosphine was added (0.13 g) and stirring was continued for 7 hours. The crude product was then isolated as described in Example 2g, then crystallized from methylene chloride:hexane (1:1) to afford 0.400 g (48%) of product: tlc, $R_f$=0.08, silica gel, ethyl acetate:hexane (1:1).

f. 2-(1-Benzyl-2-oxo-3-pyrrolin-4-yl)amino-3-(2-methylpropyl)benzonitrile (Formula II, A=formula Ia, X=N, n=1, Ra=2-methylpropyl, Rb=benzyl)

To a 0° suspension of the enamine from Example 26e (0.39g) and dry zinc bromide (0.078 g) in methylene chloride (5 ml) was added dropwise bis-(2-propyl)zinc (about 0.52 g) in methylene chloride (3 ml). After stirring 1 hour at 0° and 2 hours at ambient temperature, the mixture was quenched by pouring it slowly into excess cold aqueous saturated $NH_4Cl$. Ethyl acetate was added, the layers were separated and the aqueous layer was extracted with additional ethyl acetate. The combined organic layer was washed with brine, dried over $Na_2SO_4$ and concentrated. Purification by trituration with diethyl ether gave 0.40 g (95%) of a light yellow solid.

EXAMPLES 27-28

The process described in Example 26 was repeated for the synthesis of compounds of the formula I where A=formula Ia, Ra=2-methylpropyl, Rc=H, X=N, n=1, and Rb is selected from 2-propenyl (Example 27) and 2,4-dimethoxybenzyl (Example 28) by substituting ethyl N-(2-propenyl)glycinate and ethyl N-(2,4-dimethoxybenzyl)glycinate, respectively, for the ethyl N-benzylglycinate used in Example 26b. The Examples are listed in Table V.

TABLE V

| Example | Ra | Quinoline Yield | m.p. | Elemental Analysis |
|---|---|---|---|---|
| 27 | 2-propenyl | 83% | 165-166°* | Calculated for $C_{18}H_{21}N_3O$: C, 73.19; H, 7.17; N, 14.23 Found: C, 73.57; H, 6.91; N, 14.24 |
| 28 | 2,4-dimethoxybenzyl | 64% | 194-195°* | Calculated for $C_{24}H_{27}N_3O_3$: C, 71.09; H, 6.71; N, 10.36 Found: C, 70.75; H, 6.67; N, 10.20 |

*Recrystallized from tert-butylmethyl ether/hexane

EXAMPLE 29 a.

10-Amino-6-(2-methylpropyl)-2-(2-propenyl)1,2,3,4-tetrahydropyrido[4,5-b]quinolin-1(1H)-one (Formula I, A=formula Ia, X=N, n=2, Ra=2-methylpropyl, Rb=2-propenyl, Rc=H)

The enamine described in Example 29d (1.20 g) was added as a solution in tetrahydrofuran (3 ml) to a suspension of freshly washed sodium hydride (0.19 g, 55% in oil) in tetrahydrofuran (5 ml) at 0° C. Following the addition the mixture was warmed to ambient temperature with stirring one hour. Dry cadmium chloride (0.85 g) was added all at once and the mixture slowly warmed to 90°. At this point 5 ml of toluene was added and the mixture refluxed for 2 hours. After cooling to ambient temperature, the mixture was quenched by slowly adding excess saturated aqueous disodium ethylenediaminetetraacetic acid. After stirring several minutes the product was extracted into ethyl acetate. The ethyl acetate layer was dried ($Na_2SO_4$) and concentrated to leave a dark solid. The material was purified by silica gel column chromatography using ethyl acetate:hexane (1:1) as the eluent. The yellow solid was recrystallized from tert-butylmethyl ether/hexane to afford 0.45 g (38%) of pale yellow crystals m.p. 141°-142° tlc, $R_f$=0.58, silica gel, ethyl acetate.

b.

3-[1-(2-Propenyl)-2,4-dioxopiperidyl]amino-3-(hydroxymethyl)benzonitrile (Formula II, A=formula Ia, X=N, n=2, Ra=CHZOH, Rb=2-propenyl)

The product from Example 18d (2.57 g) was heated together with the product described in Example 2e (2.37 g) in a solvent mixture consisting of methylene chloride (15 ml) and toluene (15 ml) containing 0.09 g of p-toluenesulfonic acid. The water/toluene/ methylene chloride azeotrope was removed continuously by a Dean-Stark trap. After reaching a bath temperature of 135° at which point the volatiles had been removed, the mixture was cooled to ambient temperature. The residue was partitioned between ethyl acetate and saturated aqueous $NaHCO_3$. The ethyl acetate layer was separated, washed with brine and dried over $MgSO_4$ After concentrating, the crude product was purified by column chromatography over silica gel using ethyl acetate:hexane (1:1) as the eluent. There was obtained 4.71 g (quantitative) of a yellow oil: tlc, $R_f$=0.18, silica gel, ethyl acetate:hexane (1:1).

c.

3[1-(2-Propenyl)-2,4-dioxopiperid-4-yl)amino-3-(chloromethyl)benzonitrile (Formula IIa, A'=formula Ia, X=N, n=2, Rb=2-propenyl, Ra=chloromethyl)

The product from Example 29b (4.53 g) was stirred with triphenylphosphine (4.82 g) and $CCl_4$ (15.5 ml) in methylene chloride (50 ml) at ambient temperature. After stirring 8 hours an additional portion of triphenylphosphine (1.45 g) was added and stirring was continued for 12 additional hours. The volatiles were removed and the residue partitioned between ethyl acetate and water. The ethyl acetate layer was dried ($Na_2SO_4$) and concentrated to leave a dark brown gum. Crystallization from methylene chloride:hexane (2:3) afforded the product (2.97 g, 62%) as an offwhite solid: tlc, $R_f$=0.30, silica gel, methanol: chloroform (1:19).

d.

3-[1-(2-Propenyl)-2,4-dioxopiperid-4-yl]amino-3-(2-methylpropyl)benzonitrile (Formula II, A=formula Ia, X=N, n=1, Ra=2-methylpropyl, Rb=2-propenyl)

To a 0° suspension of the enamine from Example 29c (1.Z g) and dry zinc bromide (0.27 g) in methylene chloride (10 ml) was added dropwise bis(Z-propyl)zinc (about 1.8 g) in methylene chloride (5 ml). After stirring for 1 hour at 0° and 1 hour at ambient temperature, the mixture was quenched by pouring it slowly into excess cold aqueous saturated $NH_4Cl$. Ethyl acetate was added, the layers separated and the organic phase dried over $MgSO_4$. After concentration, the crude product was purified by column chromatography over silica gel using ethyl acetate/tetrahydrofuran as the eluent. There was obtained 1.25 g (quantitative) of product: tlc, $R_f$=0.38, silica gel, ethyl acetate.

EXAMPLE 30 a.

10-Amino-6-(2-methylbutyl)-2-(2-propenyl)-1,2,3,4-tetrahydropyrido[4,5-b]quinolin-1-(1H)-one (Formula I, A=formula Ia, X=N, n=2, Ra=2-methylbutyl, Rb=2-propenyl, Rc=H)

The enamine described in Example 30b (0.70 g) was reacted with sodium hydride (0.19 g, 55% in oil) and cadmium chloride (0.88 g) according to the procedure of Example 29a. After heating at reflux for hour, the reaction was cooled to ambient temperature and excess disodium ethylenediaminetetraacetic acid added as an aqueous solution. After stirring for 15 minutes, the product was extracted into ethyl acetate. The extracts were dried (MgSO$_4$) and concentrated. The crude product was purified by column chromatography over silica gel using ethyl acetate:hexane (1:1) as the eluent. The solid obtained was recrystallized from tert-butylmethyl ether/hexane to afford 0.70 g (54%) of the quinoline as white needles: tlc, R$_f$=0.73, silica gel, ethyl acetate: m.p. 118°-119°.

Analysis calculated for C$_{20}$H$_{25}$N$_3$O: C, 74.27: H, 7.79: N, 12.99. Found: C, 74.29: H, 7.80: N, 12.95.

b.

3-[1-(2-Propenyl)-2,4-dioxopiperid-4-yl)amino-3-(Z-methylbutyl)benzonitrile (Formula II, A=formula Ia, X=N, n=1, Ra=Z-methylbutyl, Rb=2-propenyl)

The product from Example 29c (1.30 g) was reacted with bis(2-butyl)zinc (2.13 g) and zinc bromide (0.29 g) in 10 ml of methylene chloride, according to the procedure of Example 29d. After stirring for 1 hour at 0° and 1 hour at ambient temperature, the crude product was isolated as described in Example 29d. There was obtained 1.6 g of a beige solid (quantitative): tlc, R$_f$=0.38, silica gel, ethyl acetate.

EXAMPLE 31 a.

9-Amino-2,3-dihydro-5-(3-trifluoromethylbutyl)-2-propylpyrrolo[3,4-b]quinolin-1-one (Formula I, A=formula Ia, X=N, n=1, Ra=3-trifluoromethylbutyl, Rb=propyl, Rc=H)

To a suspension of magnesium turnings (0.55 g) in diethyl ether (2 ml) at ambient temperature was added dropwise 3-trifluoromethyl-1-bromobutane (3.90 g). A little gentle warming was necessary to help initiate Grignard reagent formation. After the addition was complete the mixture was refluxed for 1 hour to ensure complete formation of the reagent. After cooling to ambient temperature the Grignard reagent was added slowly to a solution of zinc bromide (4.5 g) in tetrahydrofuran (10 ml). The thick, white mixture was stirred 2 hours at ambient temperature followed by addition of dichloro-[1,1'-bis(diphenylphosphino)ferrocene]palladium (II) (0.16 g) and stirring for an additional 5 minutes. The bromoquinoline described in Example 31 g (1.20 g) was next added and the mixture heated to reflux for 10 hours. After cooling to ambient temperature a few milliliters of saturated NH$_4$Cl (aqueous) was added followed by partitioning the mixture between aqueous disodium ethylenediaminetetraacetic acid and ethyl acetate. After stirring for 30 minutes, the layers were separated. The organic phase was washed with brine, dried (Na$_2$SO$_4$) and concentrated. The crude product was purified by column chromatography over silica gel using ethyl acetate:hexane (1:3) as the eluent. Recrystallization of the purified material from tert-butylmethyl ether/hexane afford 0.13 g (8.7%) of the desired product: tlc, R$_f$=0.40, silica gel, ethyl acetate:hexane (1:1): m.p., 118-120.

Analysis calculated for
C$_{19}$H$_{22}$N$_3$OF$_3$: C, 62.46: H, 6.07: N, 11.50. Found: C, 62.21: H, 6.03: N, 11.43.

b. 2-Bromoisonitrosoacetanilide

To a warm (40°) solution containing 1.51 Kg of Na$_2$SO$_4$.10H$_2$O and chloral hydrate (84.0 g) in 1 liter of water was added all at once a solution of 2-bromoaniline (80.5 g) in 160 ml of water also containing 40 ml of concentrated HCl. To this mixture was added hydroxylamine hydrochloride (100.8 g) in 200 ml of water. The mixture was heated to reflux with monitoring of the internal reaction temperature. After 40 minutes at 104° the reaction was cooled to ambient temperature and extracted with ethyl acetate. The extracts were dried (MgSO$_4$) and concentrated to leave a dark brown solid. The solid was triturated with methylene chloride/hexane to leave 80 g (69%) of a light brown solid; tlc, R$_f$=0.57, silica gel, ethyl acetate:hexane (2:3).

c. 7-Bromoisatin

To 250 ml of warm (about 50°) concentrated sulfuric acid was added the product described in Example 31b (80 g) in several portions. The internal temperature was maintained below 65° during the addition. After complete addition the reaction was warmed slowly to 80° stirring five minutes at 80°. The mixture was poured into excess ice/water. The resulting solid was removed by filtration and washed with water. The aqueous layer was neutralized with Na$_2$CO$_3$ and then extracted with ethyl acetate. The L extracts were dried (MgSO$_4$) and concentrated. The residue was purified by column chromatography over silica gel using ethyl acetate:hexane (1:4) as the eluent. There was obtained 3.4 g of product which was combined with the solid which had been removed by filtration. The combined product was recyrstallized from methylene chloride/ethyl acetate to afford 61.2 g (84%) of the isatin as an orange solid: m.p., 212°-214°.

d. 7-Bromoisatin oxime

The isatin (61.2 g) described in Example 31c was dissolved in ethanol (550 ml). To this was added hydroxylamine hydrochloride hydroxylaminehydrochloride in 100 ml of water. The mixture was stirred at 80° for 10 minutes, then cooled in an ice-bath. The yellow precipitate was removed by filtration and dried under high vacuum for 24 hours. There was obtained 62.3 g (95%) of the isatin oxime: tlc, R$_f$=0.20, silica gel, ethyl acetate:hexane (2:3): m.p. greater than 250°.

e. 3-Bromoanthranilonitrile

A suspension of the oxime described in Example 31d in 2.9 liters of methylene chloride was treated with 2,6-lutidine (78.1 ml) then cooled to 0° and 112 ml of trifluormethanesulfonic anhydride added. The cooling bath was removed and the mixture heated to vigorous reflux. After heating for 3 hours, complete dissolution had occurred and a dark brown solution remained. The solution was cooled to ambient temperature with a water bath and 174 ml of 1,8-diazabicyclo[5.4.0]undec-7-ene (DBU) added slowly. The internal temperature was maintained below 30° during the addition of the DBU. After stirring for 1 hour at ambient temperature, the mixture was poured slowly with vigorous stirring into excess dilute aqueous sodium bicarbonate. After stirring for several minutes the mixture was extracted with methylene chloride. The extracts were dried (MgSO$_4$) and concentrated. The crude product was purified by column chromatography over silica gel using methylene chloride as the eluent. The product was triturated with hexane, filtered and dried under vacuum to afford 64.9 g (57%) of the 3-bromoanthranilonitrile: tlc, R$_f$=0.68, silica gel, ethyl acetate:hexane (2:3); m.p. 119°-120°.

f. 2-(1-Propyl-2-oxo-3-pyrrolin-4-yl)amino-3-bromobenzonitrile (Formula II, A=formula Ia, X=N, n=1 Ra=Br, Rb=propyl)

The procedure described in Example 10f was followed except for the following changes or substitutions: the product from Example 31e (8.91 g) was used instead of 2-amino-3-pentylbenzonitrile: 3-carboethoxy-1-propyl-2,4-dioxopyrrolidine (3.19 g) was used instead of the amount indicated in Example 10f: toluene (40 ml instead of 3 ml): acetonitrile (1.5 liters instead of 400 ml): and p-toluenesulfonic acid (0.13 g). After completion of the reaction and isolation of the crude product as described in Example 10f, the product was purified by column chromatography over silica gel using ethyl acetate:hexane (1:3) as the eluent. There was obtained 2.1 g (29%) of the product as beige crystals. Unreacted 3-bromoanthranilonitrile (Example 31e) was recovered in 81% yield (7.22 g); tlc (product), $R_f$=0.13, silica gel, ethyl acetate:hexane (1:1).

g. 9-Amino-2,3-dihydro-5-bromo-2-propylpyrrolo[3,4-b]quinolin-1-one (Formula I, A=formula Ia, X=N, n=1, Ra=Br, Rb=propyl, Rc=H).

The procedure described in Example 7a was followed except for the following changes or substitutions: the enamine from Example 31f (2.22 g) was used instead of the enamine in Example 7a: NaH (0.33 g, 55% in oil instead of .17 g), tetrahydrofuran (7 ml instead of 2 ml), cadmium chloride (1.52 g instead of .81 g), dimethylformamide (0.5 ml), and toluene (7 ml instead of the amount indicated in Example 7a). After completion of the reaction and isolation of the crude product as described in Example 7a, the product was purified by column chromatography over silica gel using ethyl acetate:hexane (1:1) as the eluent. Trituration of the product with diethyl ether afforded 1.37 g (62%) of a light brown solid: tlc, $R_f$=0.24, silica gel, ethyl acetate:-hexane (1:1); m.p. 221°-226° (with decomposition).

Analysis calculated for
$C_{14}H_{14}N_3OBr$: C, 52.21: H, 4.41: N, 13.12. Found: C, 52.46: H, 4.42: N, 13.10.

EXAMPLES 32-34

The process described in Example 31a was repeated for the synthesis of compounds of formula I where A=formula Ia, Rb=propyl, Rc=H, X=N, n=1, and Ra is selected from 4,4,4-trifluorobutyl (Example 32), 4-fluorobenzyl (Example 33), and 3-butenyl (Example 34) by substituting the appropriate Grignard reagents for the 3-trifluoromethylbutylmagnesium bromide used in Example 31a. The results of these Examples are included in Table VI.

TABLE VI

| Example | Ra | Quinoline Yield | m.p. Quinoline | Elemental Analysis |
|---|---|---|---|---|
| 32 | 4,4,4-trifluorobutyl | 34% | 134–136°* | Calculated for $C_{18}H_{20}N_3OF_3$ C, 61.55; H, 5.74; N, 11.96 Found: C, 61.28; H, 5.74; N, 11.81 |
| 33 | 4-fluorobenzyl | 36% | 222–224°** | Calculated for $C_{21}H_{20}N_3OF$ C, 72.19; H, 5.77; N, 12.03 Found: C, 72.19; H, 5.79; N, 12.05 |
| 34 | 3-butenyl | 32% | 116–120°* | Calculated for $C_{18}H_{21}N_3O$ C, 73.19; H, 7.17; N, 14.23 Found: C, 72.98; H, 7.14; N, 14.21 |

*Recrystallized from tert-butylmethyl ether/hexane
**Recrystallized from ethyl acetate/hexane

EXAMPLE 35 a. 9-Amino-2,3-dihydro-5-(3-pentynyl)-2-propyl pyrrolo[3,4-b]quinolin-1-one (Formula I, A=formula Ia, X=N, n=1, Ra=3-pentynyl, Rb=propyl, Rc=H)

To a suspension of magnesium turnings (1.16 g) in tetrahydrofuran (10 ml) at 0° was added dropwise 1-bromo-3-pentyne (6.4 g). Following the addition the mixture was stirred 2 hours at 0° to ensure complete formation of the Grignard reagent. The reagent was transferred via cannula to a solution of zinc bromide (9.68 g) in tetrahydrofuran (10 ml) maintained at 0°. The thick, white mixture was warmed to ambient temperature and stirred for 30 minutes. To this was added dichloro[1,1'-bis(diphenylphosphino)ferrocene]palladium (II) (0.23 g) and the mixture was stirred for 5 minutes. The product described in Example 35d (2.0 g) was added all at once and the mixture warmed to 40°. After 2 hours the mixture was cooled and several milliliters of saturated aqueous NH₄Cl was added slowly. Excess aqueous disodium ethylenediaminetetraacetic acid was added and the mixture was stirred for 30 minutes. The reaction was extracted with ethyl acetate and the layers separated. The ethyl acetate layer was washed with brine, dried ($Na_2SO_4$) and concentrated. The crude product was purified by column chromatography over silica gel followed by recrystallization from tert-butylmethyl ether/hexane to afford 0.69 g of a crystalline solid (41%): m.p. 147°–149°.

Analysis calculated for $C_{19}H_{21}N_3O$: C, 74.24; H, 6.84; N, 13.67. Found: C, 74.09; H, 6.69; N, 13.59.

b. 3-Iodoanthranilonitrile

The processes described in Examples 31b-31e were repeated for the synthesis of 3-iodoanthranilenitrile by substituting 2-iodoaniline for 2-bromoaniline in Example 31b. The remainder of the processes (Examples 31b-e) required identical reaction conditions and proportions of reagents as described in Examples 31b-e. The product was obtained in a 27% overall yield: m.p. 122°-124°.

c. 2-(1-Propyl-2-oxo-3-pyrrolin-4-yl)amino-3-iodobenzonitrile (Formula II, A=formula Ia, X=N, n=1, Ra=iodo, Rb=propyl)

The procedure described in Example 10f was followed except for the following changes or substitutions: the product from Example 35b (20 g) was used instead of 2-amino-3-pentylbenzonitrile: 3-carboethoxy 1-propyl-2,4-dioxopyrrolidine (10 g) was used instead of the amount indicated in Example 10f; toluene (75 ml instead of 3 ml), acetonitrile (2 liters instead of 400 ml) and catalytic p-toluensulfonic acid. After completion of the reaction and isolation of the crude product as described in Example 10f, the product was purified by trituration with methylene chloride. There were obtained 5.83 g (34%) of product: tlc. $R_f$=0.16, silica gel, ethyl acetate:hexane (1:1): m.p. 165°-171°.

d.
9-Amino-2,3-dihydro-5-iodo-2-propylpyrrolo[3,4-b]quinolin-1-one (Formula I, A=formula Ia, X=N, n=1, Ra=I, Rb=propyl, Rc=H)

The procedure described in Example 7a was followed except for the following changes or substitutions: the enamine from Example 35c (5.75 g) was used instead of the enamine in Example 7b; NaH (0.8 g, 55% in oil, instead of 0.17 g), tetrahydrofuran (40 ml instead of 2 ml), cadmium chloride (3.59 g instead of 0.81 g), and toluene (10 ml instead of the amount indicated in Example 7a). After completion of the reaction and isolation of the crude product as described in Example 7a, the product was purified by trituration with methylene chloride. There was obtained 1.16 g (20%) of a light brown solid: tlc, $R_f$=0.59, silica gel, ethyl acetate:hexane (1:1): m.p.=117°-119°.

EXAMPLE 36 a. 9-Amino-2,3-dihydro-5-(2-methylpropyl)-2-(2-propenyl)cyclopenta[b]-quinolin-1-one (Formula I, with A=formula Ia, X=CH, n=1, Ra=2-methylpropyl, Rb=2-propenyl, Rc=H)

To a 0° solution of dry ZnBr2 (12.5 g) in tetrahydrofuran (25 ml) was added dropwise a solution of 2-methylpropylmagnesium chloride (27.7 ml, 2.0M in ether). The mixture was warmed to ambient temperature with stirring for 90 minutes. To this was added dichloro[1,1'-bis(diphenylphosphino)ferrocene]palladium (II) (0.20 g) and the reaction was stirred for 5 minutes. The product from Example 36c (1.76 g) was added all at once and the mixture stirred overnight at ambient temperature. After cooling to 0°, cold aqueous saturated NH4Cl was added slowly followed by disodium ethylenediominetetraacetic acid and ethyl acetate. The ethyl acetate layer was dried (MgSO4) and concentrated. The crude product was purified by column chromatography over silica gel using ethyl acetate:hexane (1:1) as the eluent. Recrystallization from tetrahydrofuran afforded an off-white powder (0.60 g, 37%); tlc, $R_f$=0.49 silica gel, ethyl acetate: hexane (1:3): m.p. 123°-124°.

Analysis calculated for C19H22N2O: C, 77.52; H, 7.53: N, 9.52. Found: C, 77.40: H, 7.58: N, 9.40.

b.
2-(1-Oxo-5-(2-propenyl)-2-cyclopenten-3-yl)amino-3-bromobenzonitrile (Formula II, A=formula Ia, X=CH, n=1, Ra=Br, Rb=2-propenyl).

The product described in Example 31e (5.0 g) was refluxed together with 4,4-dimethyl-1,3-cyclopentanedione (4.0 g, see U.S. Pat. No. 4,546,104 for a description of the synthesis) and p-toluenesulfonic acid (0.15 g) in toluene (25 ml). Evolved water was removed as the azeotrope with toluene via a Dean-Stark trap. After heating 24 hours, excess toluene was distilled off and the residue cooled to ambient temperature. The residue was partitioned between ethyl acetate and saturated aqueous NaHCO3. After separation of the layers, the ethyl acetate layer was dried (Na2SO4) and concentrated. The crude product was purified by column chromatography over silica gel using ethyl acetate:hexane (1:1) to afford the enamine (3.90 g, 48%) as a yellow solid: tlc, $R_f$=0.39, silica gel, ethyl acetate.

c.
9-Amino-5-bromo-2,3-dihydro-2-(2-propenyl)cyclopenta[b]quinolin-1-one (Formula I, A=formula Ia, X=CH, n=1, Ra=bromo, Rb=2-propenyl, Rc=H)

The product prepared in Example 36b (3.90 g) was added as a solution in tetrahydrofuran (10 ml) and Z0 dimethylformamide (1 ml) to a 0° suspension of NaH (0.59 g, 55% in oil) in tetrahydrofuran (3 ml). Following the addition, the mixture was warmed slowly to ambient temperature with stirring for 45 minutes. Cadmium chloride (2.70 g) was added and the mixture heated to gentle reflux. Toluene (10 ml) was slowly added and heating continued for 4 hours (bath temperature 110°). After cooling to ambient temperature the mixture was partitioned between ethyl acetate and aqueous disodium ethylenediaminetetraacetic acid. The layers were separated and the ethyl acetate layer was dried (MgSO4) and concentrated. The crude product was purified by column chromatography over silica gel using ethyl acetate:hexane (1:3) as the eluent. There was obtained a yellow solid (3.24 g, 83%): tlc, $R_f$=0.45, silica gel, ethyl acetate:hexane (1:1).

EXAMPLE 37

9-Amino-2,3-dihydro-5-(2,2-dimethylpropyl)-2-(2-propenyl)cyclopenta[b]quinoline-1-one (Formula I, A=formula Ia, X=CH, n=1, Ra=2,2-dimethylpropyl, Rb=2-propenyl, Rc=H)

The process described in Example 36a was repeated using the following changes or substitutions: 2,2-dimethylpropyl magnesium bromide (28.0 ml, 2.0M in ether) was used instead of 2-methylpropylmagnesium chloride. All other amounts of reagents were identical to Example 36a. After working up and isolating the crude product as described in Example 36a, the material was purified by column chromatography over silica gel using ethyl acetate:hexane (1:1) as the eluent. The product was recrystallized from tert-butylmethyl ether/hexane to afford 0.83 g, of a tan solid (49%); tlc, $R_f$=0.47, silica gel, ethyl acetate:hexane (1:1): m.p. 137°-138°.

Analysis calculated for C20H24N2O: C, 77.89; H, 7.84; N, 9.08. Found: C, 77.70: H, 7.82; N, 8.98.

EXAMPLE 38

9-Amino-2,3-dihydro-5-phenyl-2-propylpyrrolo[3,4-b]-quinolin-1-one (Formula I, A=formula Ia, X=N, n=1, Ra=phenyl, Rb=propyl, Rc=H)

To a slurry of freshly washed NaH (0.22 g, 55% in oil) in tetrahydrofuran (15 ml) was added in several portions the bromoquinoline (0.80 g) described in Example 31g. The thick yellow slurry was stirred for 45 minutes at ambient temperature, followed by the dropwise addition of trifluoroacetic anhydride (0.53 ml). The resulting solution was stirred for 10 minutes. In a separate reaction flask, phenylmagnesium bromide (12.5 ml, 2.0M in ether) was added to a solution of ZnBr2 (5-63 g) in tetrahydrofuran (10 ml). The mixture was stirred for 1 hour at ambient temperature. To the suspension containing the phenylzinc bromide reagent was added dichloro[1,1-bis(diphenylphosphino)ferrocene]-palladium (II) (0.09 g) with stirring for 5 minutes. To this mixture was added the solution containing the N-trifluoroacetyl-substituted 5-bromoquinoline. The resulting mixture was stirred for 4 hours at ambient temperature. Saturated aqueous NH₄Cl was added slowly followed by ethyl acetate. The ethyl acetate layer was separated, washed with saturated aqueous disodium ethylenediaminetetraacetic acid and then brine. After drying (MgSO₄), the solution was filtered through a small plug of diatomaceous earth (Celite) surmounted with silica gel to afford, after concentrating, a brown solid. This material was taken up in methanol (6 ml) followed by the addition of KOH (0.32 g, powdered). The solution was warmed to 60° and stirred for 7 hours. After cooling to ambient temperature, the mixture was partitioned between ethyl acetate:tetrahydrofuran (1:1) and water. The separated organic phase was washed with water, then washed with brine. After drying (Na₂SO₄) and concentrating, the crude product was purified by column chromatography over silica gel using ethyl acetate:hexane (1:1) as the eluent. There was obtained after recrystallization from ethyl acetate:diethyl ether, 0.65 g of a fluffy white solid (82%): tlc, $R_f=0.39$. silica gel, ethyl acetate:hexane (1:1): m.p. 219°-223°.

Analysis calculated for $C_{20}H_{19}N_3O.0.2\ H_2O$: C, 74.84; H, 6.09 N, 13.09. Found: C, 75.01; H, 6.10; N, 12.95.

EXAMPLES 39–42

The process described in Example 38 was repeated for the synthesis of compounds of formula I where A=formula Ia, Rb=propyl, X=N, Rc=H, n=1, and Ra is selected from 4-fluorophenyl (Example 39), 4-chlorophenyl (Example 40), (1E)-propenyl (Example 41) and 4-methoxyphenyl (Example 42) by substituting the appropriate Grignard reagent for the phenylmagnesium bromide used in Example 38. The results of these Examples are included in the following Table VII.

stead of the enamine from Example 7a; NaH (0.36 g, 55% in oil instead of .17 g), tetrahydrofuran (15 ml instead of 2 ml), cadmium chloride (1.6 g instead of 81 g), and toluene (10 ml instead of the amount indicated in Example 7a). After completion of the reaction and isolation of the crude product as described in Example 7a, the product was purified by column chromatography over silica gel using ethyl acetate:hexane (1:1) as the eluent. Recrystallization from methylene chloride/hexane afforded 1.61 g (77%)

of a white solid: m.p. 157°-158°.

Analysis calculated for $C_{19}H_{23}N_3O$: C, 73.76; H, 7.49; N, 13.58. Found: C, 73.73; H, 7.54; N, 13.58.

b. 3-(2-Methyl-1-propenyl)-2-aminobenzonitrile
(Formula IV, A=formula Ia,
Ra=2-methyl-1-propenyl)

To a warm (about 50°) suspension of magnesium turnings (0.99 g) in 3 ml tetrahydrofuran was added dropwise 2-methyl-1-bromopropene (5.54 g). The reaction became exothermic during the addition. Following addition of the bromide, the mixture was heated at 50°-60° for 1 hour. After cooling to about 30°-35°, a solution of ZnBr₂ (9.23 g) in tetrahydrofuran (20 ml) was added. The thick white mixture was stirred for 2 hours at ambient temperature, then dichloro-[1,1'-bis(diphenylphosphino)]palladium (II) (0.17 g) was added. After 5 minutes at ambient temperature, 3-iodo-2-aminobenzonitrile (the product from Example 35b (1 g)) was added in tetrahydrofuran (2 ml). The reaction mixture was stirred for 30 minutes at ambient temperature, then quenched by adding a few milliliters of saturated aqueous NH₄Cl followed by a few milliliters of aqueous disodium ethylenediaminetetraacetic acid. After stirring for 30 minutes, the mixture was extracted with methylene chloride. After washing the extracts with brine, they were dried (Na₂SO₄) and concentrated. The residue was chromatographed over silica gel using methylene chloride as the eluent to leave 0.69 g (98%) of a yellow solid; tlc, $R_f=0.40$, silica gel, CH₂Cl₂: hex-

TABLE VII

| Example | Ra | Yield | m.p. | Elemental Analysis |
|---------|------|-------|------|--------------------|
| 39 | 4-fluorophenyl | 88% | 171–183°¹ | Calculated for<br>$C_{20}H_{18}FN_3O.H_2O$: C, 68.32; H, 5.68; N, 11.95<br>Found: C, 68.48; H, 5.71; N, 11.62 |
| 40 | 4-chlorophenyl | 73% | 179–183°² | Calculated for<br>$C_{20}H_{18}N_3OCl.0.25H_2O$: C, 67.41; H, 5.23; N, 11.79<br>Found: C, 67.77; H, 5.16; N, 11.38 |
| 41 | (1E)-propenyl | 32% | 199–200°³ | Calculated for<br>$C_{17}H_{19}N_3O.0.6H_2O$: C, 69.87; H, 6.97; N, 14.38<br>Found: C, 69.79; H, 6.56; N, 14.10 |
| 42 | 4-methoxyphenyl | 59% | 181–183°⁴ | Calculated for<br>$C_{21}H_{21}N_3O_2.0.7H_2O$: C, 70.06; H, 6.27; N, 11.67<br>Found: C, 70.21; H, 6.08; N, 11.70 |

¹Recrystallized from methanol/water
²Recrystallized from ethyl acetate/tert-butyl methyl ether
³Recrystallized from ethyl acetate/methylene chloride/hexane
⁴Recrystallized from tert-butyl methyl ether/pentane

EXAMPLE 43 a.
9-Amino-2-cyclopropylmethyl-2,3-dihydro-5-(2-methylpropyl)pyrrolo[3,4-b]quinolin-1-one (Formula I, A=formula Ia, X=N, n=1, Ra=2-methylpropyl,
Rb=cyclopropylmethyl, Rc=H)

The procedure described in Example 7a was followed except for the following changes or substitutions: the enamine from Example 31d (2.19 g) was used inane (1:1).

c. 3-(2-Methylpropyl)-2-aminobenzonitrile (Formula IV, A=formula Ia, Ra=2-methylpropyl)
The product from Example 43b (9.4 g) was hydrogenated over 10% palladium on carbon (0.5 g) in ethanol (200 ml) at 3 atmospheres. After about 20 hours, the mixture was filtered through diatomaceous earth (Celite) and concentrated. Purification by column chromatography over silica gel using methylene chloride as the eluent afforded 7.8 g (78%) of product: tlc, $R_f=0.46$, $CH_2Cl_2$: hexane (1:1).

d.

2-(1-Cyclopropylmethyl-2-oxo-3-pyrrolin-4-yl)amino-3-(2-methylpropyl)benzonitrile (Formula II, A = formula Ia, X = N, n = 1, Ra = 2-methylpropyl, Rb = cyclopropylmethyl)

The procedure described in Example 10f was followed except for the following changes or substitutions: the product from Example 43c (1.6g) was used instead of 2-amino-3-pentyl-benzonitrile: 3-carboethoxy-1-cyclopropyl-2,4-dioxopyrrolidine (1.89 g, prepared according to the procedure of Examples 26b-c by substituting ethyl N-cyclopropylglycinate for ethyl N-benzylglycinate) was used instead of the 3-carboethoxy-1-propyl-2,4- dioxopyrrolidione used in Example 10f: toluene (15 ml instead of 3 ml), acetonitrile (500 ml instead of 400 ml) and catalytic p-toluenesulfonic acid. After completion of the reaction and isolation of the crude product as described in Example 10f, the product was purified by column chromatography over silica gel using ethyl acetate: hexane (1:1) as the eluent. There was obtained 2.19 g (84%) of the product: tlc, $R_f=0.43$, silica gel, ethyl acetate:hexane (1:1).

EXAMPLE 44 a.

9-Amino-2,3-dihydro-5-(2-propenyl)-2-propylpyrrolo[3,4-b]quinolin-1-one (Formula I, A = formula Ia, X = N, n = 1, Ra = 2-propenyl, Rb = propyl, Rc = H)

The procedure used in Example 7a was followed except for the following changes or substitutions: the enamine from Example 44c (1.72 g) was used instead of the enamine in Example 7a: NaH (0.29 g, 55% in oil instead of .17 g), tetrahydrofuran (6 ml instead of 2 ml), cadmium chloride (1.34 g instead of 81 g), dimethylformamide (0.5 ml) and toluene (7 ml instead of the amount indicated in Example 7a). After completion of the reaction and isolation of the crude product as described in Example 7a, the product was purified by column chromatography over silica gel using ethyl acetate:hexane (1:3 to 1:1 gradient) as the eluent. There was obtained 0.80 g (47%) of the title product: tlc, $R_f=0.30$, silica gel, ethyl acetate:hexane (1:1): m.p. 152°-152.5°.

Analysis calculated for $C_{17}H_{19}N_3O$: C, 72.57; H, 6.81; N, 14.93. Found: C, 72.28: H, 6.79: N, 14.86.

b. 3-(2-Propenyl)-2-aminobenzonitrile (Formula IV, A = formula Ia, Ra = 2-propenyl)

The procedure described in Example 43b was followed except for the following changes or substitutions: 2-bromopropene (7.3 ml) was used instead of 2-methyl-1-bromopropene: magnesium (2.19 g instead of 0.99 g), ZnBr2 (18.5 g instead of 9.23 g) tetrahydrofuran (90 ml total instead of the amount used in Example 43b), dichloro-[1,1'-bis(diphenylphosphino)ferrocene]palladium (II) (0.60 g instead of 0.17 g), and 3-iodo-2-aminobenzonitrile (5.0 g instead of the amount used in Example 43b). Following completion of the reaction and isolation of the crude product as described in Example 43b, the product was purified by column chromatography over silica gel using ethyl acetate: hexane (3:20) as the eluent. There was obtained 3.06 g (94%) of the product as a light yellow oil; tlc, $R_f=0.21$, silica gel, ethyl acetate:hexane (1:1).

c.

2-(1-Propyl-2-oxo-3-pyrrolin-4-yl)amino-3-(2-propenyl)benzonitrile (Formula II, A = formula Ia, X = N, n = 1, Ra = 2-propenyl, Rb = propyl)

The procedure described in Example 10f was followed except for the following changes or substitutions: the product from Example 44b (3.0 g) was used instead of the 2-amino-3-pentylbenzonitrile of Example 10f: 3-carboethoxy-1-propyl-2,4-dioxopyrrolidine (5.25 g instead of the amount used in Example 10f), acetonitrile (100 ml instead of the amount used in Example 10f), toluene (20 ml instead of the amount used in Example 10f) and catalytic p-toluenesulfonic acid were also used. After completion of the reaction as described in Example 10f, the crude product was purified by column chromatography over silica gel using ethyl acetate:hexane (1:1) as the eluent. There was obtained 1.72 g (32%) of product: tlc, $R_f=0.09$, silica gel, ethyl acetate:hexane (1:1).

EXAMPLE 45

9-Amino-2,3-dihydro-2-propyl-5-(2-propyl)pyrrolo[3,4-b]quinolin-1-one (Formula I, A = formula Ia, X = N, n = 1, Ra = 2-propyl, Rb = propyl, Rc = H)

The product from Example 44a (0.74 g) was hydrogenated on a Parr shaker over 5% palladium on carbon (0.10 g) in ethanol (20 ml) at about 3 atmospheres of hydrogen. After 1.5 hours the reaction was removed from the Parr shaker and filtered. After concentrating, the product was purified by column chromatography over silica gel using ethyl acetate: hexane (1:3) as the eluent. Recrystallization from tert-butylmethyl ether afforded 0.42 g (57%) of the product as white needles: tlc, $R_f=0.37$, silica gel, ethyl acetate:hexane (1:1): m.p. 177°-178°.

Analysis calculated for $C_{17}H_{21}N_3O$: C, 72.06; H, 7.47; N, 14.83. Found: C, 71.61: H, 7.42; N, 14.92.

EXAMPLE 46 a.

9-Amino-2,3-dihydro-5-(2-methyl-1-propenyl)-2-propylpyrrolo[3,4-b]quinoline-1-one (Formula I, A = formula Ia, X = N, n = 1, Ra = 2-methyl-1-propenyl, Rb = propyl, Rc = H)

To a suspension of NaH (1.31 g, 55% in oil, washed with tetrahydrofuran) in tetrahydrofuran (30 ml) at 0° was added in several solid portions, the enamine described in Example 46b (8.08 g). Following the addition the mixture was warmed to ambient temperature and stirred for 30 minutes. Dimethylformamide (1 ml) was added followed by cadmium chloride (6.0Z g). The mixture was warmed to reflux, then toluene (30 ml) was added slowly. The reaction was heated to reflux with stirring for 1 hour. After cooling to ambient temperature, saturated aqueous NH4Cl was added followed by aqueous disodium ethylenediaminetetraacetic acid. Aqueous sodium bicarbonate was added to adjust the pH to 8, then the mixture extracted with ethyl acetate/-tetrahydrofuran. The layers were separated with the organic phase dried (MgSO4) and concentrated to leave the crude product. The product was purified by column chromatography over silica gel using ethyl acetate: methylene chloride (1:3) as the eluent. Recrystallization from ethyl acetate/tert-butylmethyl ether afforded 3.67 g (45%) of the product; tlc, $R_f$=0.29, silica gel, ethyl acetate: hexane (1:1): m.p. 219°–220°.

Analysis calculated for $C_{18}H_{21}N_3O$: C, 73.19; H, 7.17; N, 14.23. Found: C, 72.85; H, 7.12; N, 13.57.

b.
2-(1-Propyl-2-oxo-3-pyrrolin-4-yl)amino-3-(2-methyl-1-propenyl)benzonitrile (Formula II, A=formula Ia, X=N, n=1, Ra=2-methyl-1-propenyl, Rb=propyl)

Freshly prepared 1-propyl-2,4-dioxopyraolidione (prepared by heating 3-carboethoxy-1-propyl-2,4-dioxopyrrolidine (17.43 g) in acetonitrile (3 liters) as described in Example 1e) was dissolved in toluene (30 ml) and added dropwise over a 1 hour period to a refluxing mixture of the product described in Example 43b (6.5 g) and p-toluenesulfonic acid (0.22 g) in toluene (30 ml). The toluene/water azeotrope removed the water via a Dean-Stark trap. After heating for 4 hours the excess toluene was distilled off and the reaction mixture cooled to ambient temperature. The enamine product precipitated out as the reaction cooled and was removed by filtration to afford 6.12 g. The filtrate was extracted with ethyl acetate which was washed with aqueous saturated NaHCO$_3$ and dried (MgSO$_4$). After filtering and concentrating, the residue was purified by column chromatography over silica gel using ethyl acetate: hexane (1:1) as the eluent. There was obtained an additional 1.44 g of product for a combined yield of 68% (7.56 g): tlc, $R_f$=0.11, silica gel, ethyl acetate: hexane (1:1).

EXAMPLES 47-56

The process described in Example 46 was repeated for the synthesis of compounds of formula I where A=formula Ia, Ra=2-methyl-1-propyl, Rc=H, X=N, n=1, and Rb=the values listed in Table VIII under the column heading Rb. The required 3-carboethoxy-1-substituted-2,4-pyrrolidiones were obtained by the process described in Examples 26b-c by substituting the appropriate ethyl N-substituted glycinate for ethyl N-benzyleglycinate used in Examples 26b-c. The results of these Examples are included in Table VIII.

TABLE VIII

| Example | Ra | Rb | Enamine Yield | Quinoline Yield | m.p. Quinoline | Elemental Analysis for Quinoline |
|---|---|---|---|---|---|---|
| 46 | 2-methyl-1-propenyl | propyl | 27 | 45 | 219–220°*dec | Calculated for $C_{18}H_{21}N_3O$ C, 73.19; H, 7.17, N, 14.23 Found: C, 72.85; H, 7.12; N, 13.57 |
| 47 | 2-methyl-1-propyl | butyl | 71 | 61.5 | 151–152°** | Calculated for $C_{19}H_{25}N_3O$ C, 73.28; H, 8.09; N, 13.49 Found: C, 72.98, H, 8.05; N, 13.26 |
| 48 | 2-methyl-1-propyl | 3-chlorobenzyl | >99 | 82.9 | 168–170°** | Calculated for $C_{22}H_{22}N_3OCl$ C, 69.56; H, 5.84; N, 11.06 Found: C, 69.22, H, 5.95; N, 10.90 |
| 49 | 2-methyl-1-propyl | 2-methoxyethyl | 63.8 | 68 | 139–142°** | Calculated for $C_{18}H_{23}N_3O_2 \cdot 0.1H_2O$ C, 68.59; H, 7.42; N, 13.33 Found: C, 68.39; H, 7.38; N, 13.39 |
| 50 | 2-methyl-1-propyl | 4-fluorobenzyl | 74 | 97 | 170–172.5°*** | Calculated for $C_{22}H_{22}N_3OF$ C, 72.71; H, 6.10; N, 11.56 Found: C, 72.38; H, 6.16; N, 11.36 |
| 51 | 2-methyl-1-propyl | 4-methoxybenzyl | 89 | 63.2 | 170–173°** | Calculated for $C_{23}H_{25}N_3O_2$ C, 73.58; H, 6.71; N, 11.19 Found: C, 73.33; H, 6.68; N, 11.09 |
| 52 | 2-methyl-1-propyl | 4-chlorobenzyl | 87.4 | 70.2 | 188–190°** | Calculated for $C_{22}H_{22}N_3OCl$ C, 69.56; H, 5.84; N, 11.06 Found: C, 69.48; H, 5.93; N, 10.98 |
| 53 | 2-methyl-1-propyl | 3-methoxybenzyl | 86 | 74.4 | 149–150°** | Calculated for $C_{23}H_{25}N_3O_2$ C, 73.58; H, 6.71; N, 11.19 Found: C, 73.17; H, 6.72; N, 11.59 |
| 54 | 2-methyl-1-propyl | 2-flourobenzyl | 82.5 | 59 | 168–171°** | Calculated for $C_{22}H_{22}N_3OF$ C, 72.71; H, 6.10, N, 11.56 Found: C, 72.60; H, 6.29; N, 11.55 |
| 55 | 2-methyl-1-propyl | 3-methoxypropyl | 74 | 90.7 | 123–124°** | Calculated for $C_{19}H_{25}N_3O_2$ C, 69.70; H, 7.70; N, 12.83 Found: C, 69.59; H, 7.90; N, 12.75 |
| 56 | 2-methyl-1-propyl | 2-furylmethyl | 98.4 | 64 | 165–167°** | Calculated for $C_{20}H_{21}N_3O_2$ C, 71.62; H, 6.31; N, 12.53 Found: C, 71.43; H, 6.27; N, 12.51 |

*Recrystallized from ethyl acetate/tert-butylmethyl ether
**Recrystallized from methylene chloride/hexane
***Recrystallized from tert-butylmethylether/hexane

EXAMPLE 57 a.
9-Amino-2,3-dihydro-2-(2-propynyl)-5-(2-methylpropyl)pyrrolo[3,4-b]quinolin-1-one (Formula I, A=formula Ia, X=N, n=1, Ra=2-methylpropyl, Rb=2-propynyl, Rc=H)

To a suspension of NaH (0.395 g, 55% in oil, prewashed with hexane) in dimethylsulfoxide (5 ml) was added slowly the product described in Example 57b (2.0 g) dissolved in warm (35°) dimethylsulfoxide (20 ml). The mixture was stirred for 1 hour at 35° then added to a second flask containing 2-propynyl bromide (1.04 ml of an 80% solution in toluene) in dimethylsulfoxide (5 ml). The reaction mixture was heated at 35° for 2 hours then cooled to ambient temperature and quenched by pouring into dilute aqueous NH$_4$Cl. The mixture was extracted with ethyl acetate with the organic phase washed once with water, then brine. After drying (MgSO$_4$) and concentrating, the crude product was chromatographed over silica gel using ethyl acetate: hexane (1:1) as the eluent. Recyrstallizatoin from ethyl acetate/hexane afforded 0.55 g (24%) of a white solid: tlc, $R_f$=0.62, silica gel, ethyl acetate:hexane (1:1): m.p. 198°–199°.

Analysis calculated for $C_{18}H_{19}N_3O$: C, 73.69; H, 6.53; N, 14.32. Found: C, 73.45; H, 6.50; N, 13.99.

b

9-Amino-5-(2-methylpropyl)-2,3-dihydropyrrolo[3,4-b]quinolin-1-one (Formula I, A=formula Ia, X=N, n=1, Ra=2-methylpropyl, Rc=H, Rb=H)

The product from Example 28a (1.0 g) was dissolved in trifluoroacetic acid (40 ml) followed by warming to 40°. After stirring at 40° for 1.5 hours, the volatiles were removed and the residue partitioned between ethyl acetate/methanol and aqueous NaHCO$_3$. The organic layer was separated, concentrated and dried under high vacuum overnight to afford 0.35 g (44%) of product.

EXAMPLE 58 a.

9-Amino-2-cyclopropylmethyl-2,3-dihydro-5-propyl-pyrrolo[3,4-b]quinolin-1-one (Formula I, A=formula Ia, X=N, n=1, Ra=propyl, Rb=cyclopropylmethyl, Rc=H)

The procedure described in Example 7a was followed except for the following changes or substitutions: the enamine from Example 58d (1.3 g) was used instead of the enamine from Example 7a; NaH (0.22g, 55% in oil instead of 0.17 g), tetrahydrofuran (7.5 ml instead of the amount indicated in Example 7a), cadmium chloride (1.01 g instead of .81 g) and toluene (5 ml instead of the amount indicated in Example 7a). After completion of the reaction and isolation of the crude product as described in Example 7a, the product was purified by column chromatography over silica gel using ethyl acetate:hexane (2:3) as the eluent. Recyrstallization from tert-butylmethyl ether afforded 1.02 g (79%) of product; tlc, R$_f$=0.48, silica gel, ethyl acetate:hexane (1:1); m.p. 128°-130°.

Analysis calculated for $C_{18}H_{21}N_3O$: C, 72.75; H, 7.19; N, 14.14. Found: C, 72.70; H, 7.10; N, 14.16.

b. 3-(1-Propenyl)-2-aminobenzonitrile (Formula IV, A=formula Ia, Ra=1-propenyl)

The procedure described in Example 43b was followed with the following changes or substitutions: 1-bromopropene (6.14 ml of an E,Z-mixture instead of the 2-methyl-1-bromopropene used in Example 43b), magnesium (1.92 g instead of 0.99 g), ZnBr$_2$ (16.15 g instead of 9.23 g), dichloro-[1,1-bis(diphenylphosphino)ferrocene]palladium (II) (0.42 g instead of 0.17 g), tetrahydrofuran (47 ml instead of the amount used in Example 43b) and 3-iodo-2-aminobenzonitrile (3.5g, described in Example 35b) were used. After completion of the reaction and isolation of the crude product as described in Example 43b, the product was purified by column chromatography over silica gel using ethyl acetate:hexane (3:17) to afford 2.20 g (97%) of a light yellow oil; tlc, R$_f$=0.32, silica gel, ethyl acetate:hexane (3:17).

c. 3-Propyl-2-aminobenzonitrile (Formula IV, A=formula Ia, Ra=propyl)

The product from Example 58b (2.20 g) was hydrogenated over 10% palladium on carbon (0.176 g) in ethanol (25 ml) at about 3 atmospheres. After 1 hour at ambient temperature the mixture was filtered and concentrated to leave an oil. Purification by column chromatography over silica gel afforded 2.20 g (98%) of a low melting solid; tlc, R$_f$=0.38, silica gel, ethyl acetate:hexane (3:17); m.p. about 33°.

d.

2-(1-Cyclopropylmethyl-2-oxo-3-pyrrolin-4-yl)amino-3-propyl-benzonitrile (Formula II, A=formula Ia, X=N, n=1, Ra=propyl, Rb=cyclopropylmethyl)

The procedure described in Example 10f was followed except for the following changes or substitutions: the product from Example 58c (0.85 g) was used instead of 2-amino-3-pentyl-benzonitrile used in Example 10f; 3-carboethoxy-1-cyclopropyl-2,4-dioxopyrrolidione (1.8 g, prepared according to the procedure of Examples 26b-c by substituting ethyl N-cyclopropylmethylglycinate for ethyl N-benzylglycinate) was used instead of 3-carboethoxy-1-propyl-2,4-dioxopyrrolidione used in Example 10f; toluene (15 ml instead of the amount used in Example 10f) and catalytic p-toluenesulfonic acid. After completion of the reaction and isolation of the crude product as described in Example 10f, the product was purified by column chromatography over silica gel using ethyl acetate:hexane (1:1) as the eluent. There was obtained 1.31 g (84%) of the product; tlc, R$_f$=0.1, silica gel, ethyl acetate:hexane (1:1).

EXAMPLES 59-61

The processes described in Examples 58a through 58d were repeated for the synthesis of compounds of formula I where A=formula Ia, Ra=propyl, Rc=H, X=N, n=1, and Rb is selected from 2-propenyl (Example 59), 4-methoxybenzyl (Example 60), and 2-furylmethyl (Example 61) by substituting the appropriate ethyl N-substituted glycinates for ethyl N-benzylglycinate in Examples 26b-c for the synthesis of 3-carboethoxy-1-substituted-2,4-dioxopyrrolidiones. 2,4-dioxopyrrolidiones in Example 58d for 3-carboethoxy-1-cyclopropylmethyl-2,3-dioxopyrrolidione gives intermediates of the formula II where A=formula Ia, Ra=propyl, X=N, n=1, and Rb=the values stated above for Examples 59-61. The results of these Examples are included as shown in in Table IX.

TABLE IX

| Example | Ra | Rb | Enamine Yield | Quinoline Yield | m.p. Quinoline | Elemental Analysis for Quinoline |
|---|---|---|---|---|---|---|
| 59 | propyl | 2-propenyl | 89 | 95* | 144-145° | Calculated for $C_{17}H_{19}N_3O$ C, 72.57; H, 6.81; N, 14.93 Found: C, 71.78; H, 6.74; N, 14.76 |
| 60 | propyl | 4-methoxybenzyl | 81 | 70** | 166-167° | Calculated for $C_{22}H_{23}N_3O_2$ Found: C, 72.57; H, 6.45; N, 11.90 |
| 61 | propyl | 2-furylmethyl | 84 | 70* | 144-149° | Calculated for $C_{19}H_{19}N_3O_2$ C, 71.01; H, 5.96; N, 13.07 Found: C, 70.95; H, 6.08; N, 13.10 |

*Recrystallized from methylene chloride/hexane
**Recrystallized from ethyl acetate

EXAMPLE 62 a. 9-Amino-5-butyl-2,3-dihydro-2-(2-propenyl)pyrrolo[3,4-b]quinolin-1-one (Formula I, A=formula Ia, X=N, n=1, Ra=butyl, Rb=2-propenyl, Rc=H)

The procedure described in Example 7a was followed except for the following changes or substitutions: the enamine from Example 6Zd (1.0 g) was used instead of the enamine from Example 7a: NaH (0.17 g, 55% in oil), tetrahydrofuran (8.0 ml instead of the amount indicated in Example 7a), cadmium chloride (0.78 g instead of .81 g): dimethylformamide (2 ml) and toluene (5 ml instead of the amount indicated in Example 7a) were also used. After completion of the reaction and isolation of the crude product as described in Example 7a, the product was purified by column chromatography over silica gel using ethyl acetate:hexane (2:3) as the eluent. Recrystallization from methylene chloride/hexane afforded 0.91 g (84%) of the product: tlc, $R_f$=0.51, silica gel, ethyl acetate:hexane (1:1): m.p. 152°–153°.

Analysis calculated for $C_{18}H_{21}N_3O$: C, 73.19: H, 7.17; N, 14.23. Found: C, 73.30: H, 7.11 N, 14.28.

b. 3-(1-Butenyl)-2-aminobenzonitrile (Formula IV, A=formula Ia, Ra=1-butenyl)

The procedure described in Example 43b was followed with the following changes or substitutions: 1-bromobutene (9.9 g of an E,Z mixture) instead of 2-methyl-1-bromopropene, magnesium (1.9 g instead of 0.99 g), ZnBr2 (16.6 g instead of 9.23 g), dichloro[1,1'-bis(diphenylphosphino)ferrocene]palladium (II) (0.47 g instead of 0.17 g), tetrahydrofuran (115 ml instead of the amount used in Example 43b) and 3-iodo-2-aminobenzonitrile (4.5 g, prepared as described Example 35b). After completion of the reaction and isolation of the crude product as described in Example 43b, the product was purified by column chromatography over silica gel using methylene chloride:hexane (1:1) as the eluent. There was obtained 3.0 g (quantitative): tlc, $R_f$=0.38, silica gel, methylene chloride: hexane (1:1).

c. 3-Butyl-2-aminobenzonitrile (Formula IV, A=formula Ia, Ra=butyl)

The product from Example 62b (3.0 g) was hydrogenated over 10% palladium on carbon (0.16 g) in ethanol (60 ml) at about 3 atmospheres. After 1 hour at ambient temperature, the mixture was filtered and concentrated to leave an oil. Purification by column chromatography over silica gel afforded 2.95 g (96%) of an oil: tlc, $R_f$=0.38, silica gel, ethyl acetate:hexane (3:17).

d. 2(1-(b 2-Propenyl)-2-oxo-3-pyrrolin-4-yl)amino-3-butylbenzonitrile (Formula II, A=formula Ia, X=N, n=1, Ra=butyl, Rb=Z-propenyl)

The procedure described in Example 10f was followed except for the following changes or substitutions: the product from Example 62c (0.75 g) was used instead of 2-amino-3-pentylbenzonitrile: 3-carboethoxy-1-(2-propenyl)-2,4-dioxopyrrolidione (1.36 g prepared according to the procedure of Examples 26b-c by substituting ethyl N-(2-propenyl)glycinate for ethyl N-benzylglycinate, was used instead of 3-carboethoxy-1-propyl-2,4-dioxopyrrolidione), toluene (15 ml instead of the amount used in Example 10f) and catalytic p-toluenesulfonic acid. After completion of the reaction and isolation of the crude product as described in Example 10f, the product was purified by column chromatography over silica gel using ethyl acetate:hexane (2:1) as the eluent. There was obtained 0.75 g (59%) of the product: tlc, $R_f$=0.20, silica gel, ethyl acetate:hexane (1:1).

EXAMPLES 63-64

The processes described in Examples 62a and 62d were repeated for the synthesis of compounds of formula I where A=formula Ia, Ra=butyl, Rc=H, X=N, n=1, and Rb is selected from cyclopropylmethyl (Example 63) and 2-furylmethyl (Example 64) by substituting the appropriate ethyl N-substituted glycinates for ethyl N-benzylglycinate as described in Examples 26b-c for the synthesis of 3-carboethoxy1-substituted-2,4-dioxopyrrolidiones. Substitution of these 3-carboethoxy-1-(2-propenyl)-2,4-dioxopyrrolidione affords intermediates of formula II where A=formula Ia, Ra=butyl, X=N, n=1 and Rb=the values stated above for Examples 63-64. The results of these Examples are included in Table X.

TABLE X

| Example | Ra | Rb | Enamine Yield | Quinoline Yield | m.p. Quinoline | Elemental Analysis for Quinoline |
|---------|------|------------------|-------|------|------------|-------------------------------------------------|
| 63 | butyl | cyclopropylmethyl- | 86 | 78 | 143–144°* | Calculated for $C_{19}H_{23}N_3O$: C, 73.76; H, 7.49; N, 13.58 Found: C, 73.67; H, 7.46; N, 13.54 |
| 64 | butyl | 2-furylmethyl | 83.7 | 69 | 152-143°* | Calculated for $C_{20}H_{21}N_3O_2$: C, 71.62; H, 6.31; N, 12.53 Found: C, 71.48; H. 6.38; N, 12.51 |

*Recrystallized from methyl chloride/hexane

EXAMPLE 65 a. 9-Amino-2,3-dihydro-5-(4-methylphenyl)-2-propylpyrrolo[3,4-b]quinolin-1-one (Formula I, A=formula Ia, X=N, n=1, Ra=4-methylphenyl, Rb=propyl, Rc=H)

The procedure used in Example 7a was followed except for the following changes or substitutions: the enamine from Example 65c (0.82 g) was used instead of the enamine in Example 7a: NaH (0.12 g, 55% in oil instead of 0.17 g), tetrahydrofuran (10 ml instead of Z ml), cadmium chloride (.054 g instead of 0.81 g), dimethylformamide (2 ml) and toluene (8 ml instead of the amount indicated in Example 7a). After completion of the reaction and isolation of the crude product as described in Example 7a, the product was purified by column chromatography over silica gel using ethyl acetate:hexane (1:1) as the eluent. Recrystallization from ethyl acetate/tert-butylmethyl ether/hexane afforded 0.65 g (79%) of a fluffy white solid: tlc, $R_f$=0.18, silica gel, ethyl acetate:hexane (1:1): m.p. 215°-217°.

Analysis calculated for $C_{21}H_{21}N_3O$: C, 76.11; H, 6.39; N, 12.68. Found: C, 75.92; H, 6.53; N, 12.60.

b. 3-(4-Methylphenyl)-2-aminobenzonitrile (Formula IV, A=formula Ia, Ra=4-methylphenyl)

To a −78° solution of 4-bromotoluene (1.97 ml) in tetrahydrofuran (20 ml) was added dropwise n-butyllithium (8.9 ml, 1.87M in hexane). After stirring for 30 minutes at −78° a solution of $ZnBr_2$ (3.96 g) in tetrahydrofuran (20 ml) was added quickly. The solution was warmed to ambient temperature then stirred for 1 hour. Dichloro-1,1'-bis[(diphenylphosphino)ferrocene]palladium (II) (0.16 g) was added and the mixture was stirred for 5 minutes. To this was added 3-iodo-2-aminobenzonitrile (1.3 g, described in Example 35b as a solution in tetrahydrofuran (3 ml). After stirring for 15 minutes at ambient temperature, aqueous $NH_4Cl$ was added followed by aqueous disodium ethylenediaminetetraacetic acid, ethyl acetate and enough aqueous $NaHCO_3$ to adjust the pH to 8. The layers were separated. The organic phase was washed with saturated aqueous disodium ethylenediaminetetraacetic acid then dried over $MgSO_4$. After filtering and concentrating, the product was purified by column chromatography over silica gel using ethyl acetate:hexane (1:9) and the eluent. There was obtained 0.80 g (72%) of a crystalline solid: tlc, $R_f$=0.61, silica gel, ethyl acetate:hexane (3:17).

c. 2-(1-Propyl-2-oxo-3-pyrrolin-4-yl)amino-3-(4-methylphenyl)benzonitrile (Formula II, A=formula Ia, X=N, n=1, Ra=4-methylphenyl, Rb=propyl)

The procedure described in Example 10f was followed except for the following changes or substitutions: the product from Example 65b (0.70 g) was used instead of the 2-amino-3-pentyl-benzonitrile used in Example 10f: 3-carboethoxy-1-propyl-2,4-dioxopyrrolidine (1.07 g instead of the amount used in Example 10f): acetonitrile (250 ml instead of the amount indicated in Example 10f); toluene (5 ml instead of the amount used in Example 10f) and catalytic p-toluenesulfonic acid. After completion of the reaction as described in Example 10f, the crude product was purified by column chromatography over silica gel using ethyl acetate:hexane (1:1) as the eluent. There was obtained 0.82 g (74%) of an off-white solid: tlc, $R_f$=0.09, silica gel, ethyl acetate:hexane (1:1).

EXAMPLE 66°–68

The process described in Example 65 was repeated for the synthesis of compounds of formula I where A=formula Ia, Rb=propyl, Rc=H, X=N, n=1, and Ra is selected from 3-methoxyphenyl (Example 66), 2-methoxyphenyl (Example 67), and 4-N,N-dimethylaminophenyl (Example 68) by substituting the aryl bromides 3-bromoanisole (Example 66), 2-bromoanisole (Example 67) and 4-bromo-N,N-dimethylaniline (Example 68), respectively, for 4-bromotoluene used in Example 65. The results of these Examples are shown in Table XI.

TABLE XI

| Example | Yield Anthranilonitrile | Enamine Yield | Quinoline Yield | Quinoline m.p. | Elemental Analysis of Quinoline |
|---|---|---|---|---|---|
| 66 | 94% | 50% | 76% | 189–190°* | Calculated for $C_{21}H_{21}N_3O_2$: C, 72.60; H, 6.09; N, 12.10 Found: C, 72.75; H, 6.30; N, 12.13 |
| 67 | 62% | 85% | 56% | 187–187.5°* | Calculated for $C_{21}H_{21}N_3O_2 \cdot 0.3H_2O$: C, 71.32; H, 6.31; N, 11.24 Found: C, 71.21; H, 6.38; N, 11.18 |
| 68 | >99% | 78% | 50% | 217–221°* | Calculated for $C_{22}H_{24}N_4O$: C, 73.31; H, 6.71; N, 15.54 Found: C, 72.66; H, 6.82; N, 15.90 |

Recrystallized from tert-butylmethyl ether/hexane

EXAMPLE 69 a.

9-Amino-2,3-dihydro-5-(1-hydroxy-3-methylbutyl)-2-propylpyrrolo[3,4-b]quinolin-1-one (Formula I, A=formula Ia, X=N, n=1, Ra=1-hydroxy-3-methylbutyl, Rb=propyl, Rc=H)

To a −45° suspension of the product described in Example 69b (0.96 g) was added dropwise 2-methylpropylmagnesium chloride (3.56 ml, 2M solution in ether). Following the addition the mixture was warmed to 0° and stirred for 1 hour. The reaction was poured slowly with stirring into excess saturated $NH_4Cl$ then extracted with ethyl acetate. The extracts were dried ($MgSO_4$) and concentrated. The crude product was purified by column chromatography over silica gel using ethyl acetate:hexane (1:1) as the eluent. Recrystallization from tert-butylmethyl ether afforded 0.54 g (46%) of a yellow solid: tlc, $R_f$=0.22, silica gel, ethyl acetate:hexane (1:1): m.p. 135°-148°.

Analysis calculated for $C_{19}H_{25}N_3O_2$: C, 69.70; H, 7.70; N, 12.83. Found: C, 69.71; H, 7.80; N, 12.38.

b.

9-Amino-2,3-dihydro-2-propylpyrrolo[3,4-b]quinolin-1-one-5-carboxaldehyde (Formula I, A=formula Ia, X=N, n=1, Rb=propyl, Ra=CHO, Rc=H)

The product described in Example 41 (1.0 g) was ozonized at −78° in a mixture of methanol (7.5 ml) and methylene chloride (3 ml). Following completion of the ozonolysis) the cooling bath was removed and aqueous sodium sulfite (0.11 g in 3 ml of water) was added all at once. The mixture was warmed to ambient temperature and stirred for 1 hour. The mixture was extracted with methylene chloride. The extracts were dried ($MgSO_4$) and filtered through a short silica gel plug. After concentrating, there was obtained 0.90 g (quantitative) of the aldehyde: tlc, $R_f$=0.15, silica gel, ethyl acetate:hexane (1:1).

EXAMPLE 70–72

The process described in Example 69 was repeated for the synthesis of compounds of formula I where A=formula Ia, Rb=propyl, Rc=H, X=N, n=1, and Ra is selected from 1-hydroxyphenylmethyl (Example 70), 1-hydroxy-2-methylpropyl (Example 71), and 1-hydroxypropyl (Example 72) by substituting the Grignard reagents phenylmagnesium bromide (Example 70), 2-propylmagnesium chloride (Example 71) and ethylmagnesium bromide (Example 72), respectively, for the 2-methylpropylmagnesium chloride used in Example 69a. The results of these Examples are shown in Table XII.

TABLE XII

| Example | Yield | m.p. | Elemental Analysis |
|---|---|---|---|
| 70 | 56% | 225–232°* | Calculated for $C_{21}H_{21}N_3O$: C, 72.60; H, 6.09; N, 12.09<br>Found: C, 71.78; H, 6.07; N, 12.03 |
| 71 | 23% | 156–157°** | Calculated for $C_{18}H_{23}N_3O_2$: C, 68.98; H, 7.48; N, 13.41<br>Found: C, 68.32; H, 7.30; N, 13.77 |
| 72 | 43% | 176–177°*** | Calculated for $C_{17}H_{21}N_3O_2$: C, 68.21; H, 7.07; N, 14.04<br>Found: C, 68.11; H, 7.06; N, 14.05 |

*Recrystallized from tert-butylmethyl ether
**Recrystallized from ethyl acetate/tert-butylmethyl ether
***Recrystallized from tert-butylmethyl ether

EXAMPLE 73

The following illustrates representative pharmaceutical dosage forms which may be used for the therapeutic or prophylactic administration of a compound of formula I or of a pharmaceutically acceptable salt thereof (hereinafter referred to as 'Compound A'):

| a. Tablet 1 | mg/tablet |
|---|---|
| 'Compound A' | 5 |
| Lactose | 88 |
| Magnesium stearate | 1 |
| Polyvinylpyrrolidone | 2 |
| Sodium starch glycollate | 4 |

The lactose, sodium starch glycollate and polyvinylpyrrolidone are mixed in a planetary mixer and water added until a suitable mass for granulation is obtained. The mass obtained is granulated through a suitable size mesh and dried to obtain the optimum moisture content. The magnesium stearate is then added and the dry granulate is then passed through a further screen before final blending and compression to yield tablets each weighing 100 mg.

| b. Tablet 2 | mg/tablet |
|---|---|
| 'Compound A' | 250 |
| Lactose | 122 |
| Magnesium stearate | 4 |
| Polyvinylpyrrolidone | 8 |
| Sodium starch glycollate | 16 |

The tablets are formulated as described in part a. to yield tablets each weighing 400 mg.

| c. Tablet 3 | mg/tablet |
|---|---|
| 'Compound A' | 100 |
| Lactose | 86 |
| Magnesium stearate | 2 |
| Polyvinylpyrrolidone | 4 |
| Sodium starch glycollate | 8 |

The tablets are formulated as described in part a. to yield tablets each weighing 200 mg.

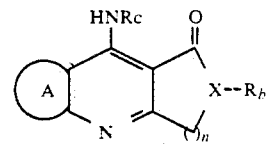

I

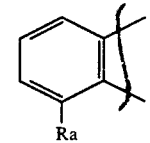

Ia

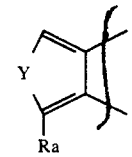

Ib

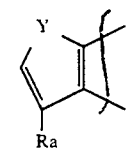

Ic

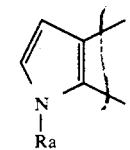

Id

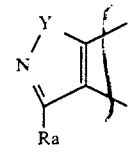

Ie

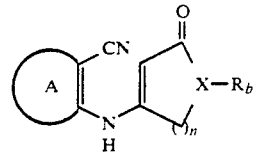

II

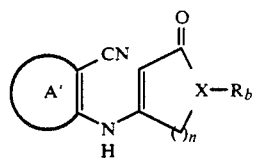

IIa

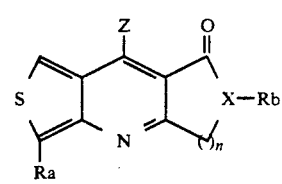

III

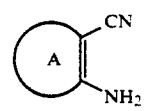

IV

-continued

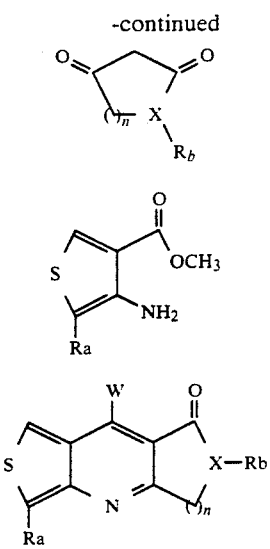

What is claimed is:
1. A compound of the following formula

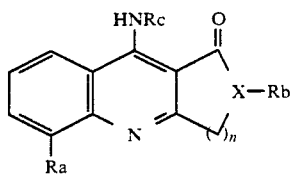

wherein:
n=2;
X=N;
Ra is selected from the group consisting of (1–10C)alkyl, (3–10C)alkenyl, (3–10C)alkynyl, (4–10C)cycloalkylalkyl, (2–10C)hydroxyalkyl, (1–10C)haloalkyl having one to about three halo group(s) independently selected from the group consisting of fluoro and chloro, (6–10C)aryl, (7–12C)arylalkyl (wherein said aryl portion of the aryl or arylalkyl is optionally substituted by a member selected from the group consisting of (1–4C)alkyl, (1–4C)alkoxy, halogeno and amino optionally substituted by one or two independently selected (1–4C)alkyl groups), and wherein the alkyl portion of the arylalkyl is optionally substituted by hydroxy, and furylmethyl or thienylmethyl wherein the heteraryl is optionally substituted by (1–3C)alkyl;

Rb is selected from the group consisting of (1–10C)alkyl (optionally substituted by (1–3C)alkoxy), (4–10C)cycloalkylalkyl, (3–8C)alkenyl, (3–8C)alkynyl, (2–8C)haloalkyl having 1-3 halo group(s) independently selected form fluoro and chloro, (2–8C)hydroxyalkyl, phenyl, phenyl(1–3C)alkyl, (wherein the phenyl portion of phenyl or phenylalkyl is optionally substituted by a member selected from the group consisting of halogeno, (1–3C)alkyl and (1–3C)alkoxy), a heteroaryl(1–3C)alkyl, wherein the heteroaryl portion is furyl or thienyl and is optionally substituted by (1–3C)alkyl; and Rc is selected from the group consisting of hydrogen, (1–10C)alkyl and (2–10C)alkanoyl;

or a pharmaceutically acceptable acid addition salt thereof.

2. A compound as claimed in claim 1 wherein:

Ra is selected from the group consisting of (1–6C)alkyl, (4–8C)cycloalkylalkyl, (3–6C)alkenyl, (3–6C)alkynyl, (6–10C)aryl, (7–12C)arylalkyl (wherein the aryl portion of the aryl or arylalkyl is optionally substituted by (1–3C)alkyl, (1–3C)alkoxy, halogeno, or amino optionally substituted by 1 or 2 independently selected (1–3C)alkyl groups, and wherein the alkyl portion of the arylalkyl is optionally substituted by hydroxy); (1–6C)haloalkyl having one to about three fluoro or chloro group(s), (3–6C)hydroxyalkyl, (4–8C)hydroxycycloalkylalkyl, and furylmethyl or thienylmethyl optionally substituted by (1–3C)alkyl;

Rb is selected from the group consisting of (2–5C)alkyl optionally substituted by (1–3C)alkoxy, (3–5C)alkenyl, (3–5C)alkynyl, (4–6C)cycloalkylalkyl, (3–5C)haloalkenyl having 1-3 halo group(s), phenyl, phenyl(1–3C)alkyl, (wherein the phenyl portion of phenyl or phenylalkyl is optionally substituted by a member selected from the group consisting of halogeno, (1–3C)alkyl and (1–3C)alkoxy), heteroaryl(1–3C)alkyl wherein the heteroaryl portion is furyl or thienyl and is optionally substituted by (1–3C)alkyl; and Rc is selected from the group consisting of hydrogen, (1–6C)alkyl and (2–6C)alkanoyl.

3. A compound as claimed in claim 2 wherein:

Ra is selected form the group consisting of (1–6)alkyl, (4–8C)cycloalkylalkyl, (3–6C)alkenyl, (3–6C)alkynyl, phenyl, phenyl(1–2C)alkyl (wherein the phenyl or the phenyl portion of the phenylalkyl is optionally substituted by a member selected from the group consisting of fluorine, chlorine, bromine, methyl, ethyl, propyl, methoxy, ethoxy, propoxy, and amino optionally substituted by 1 or 2 independently selected (1–3C)alkyl groups, and wherein the alkyl portion of the phenylalkyl is optionally substituted by hydroxy), heteroarylalkyl selected from the group consisting of 2-thienylmethyl, 3-thienylmethyl;

Rb is selected form the group consisting of (2–5C)alkyl optionally substituted by (1–3C)alkoxy, (3–5C)alkenyl, (3–5C)alkynyl, (4–6C)cycloalkylalkyl, benzyl optionally substituted on the phenyl by a member selected from the group consisting of fluorine, chlorine, bromine, (1–3C)alkyl and (1–3C)alkoxy, and 2-furylmethyl; and Rc is selected from the group consisting of hydrogen, propyl, butyl, acetyl, butyryl and valeryl.

4. A compound as claimed in claim 1 wherein:

Ra is selected from the group consisting of methyl, ethyl, n-propyl, n-butyl, 3-methylbutyl, n-pentyl, 2-methylbutyl, 2,2-dimethylpropyl, 2-methylpropyl, 3-trifluoromethylbutyl, 4,4,4-trifluorobutyl, 1-hydroxy-3-methylbutyl, 1-hydroxypropyl, 3-butenyl, 1-propenyl, 2-propenyl, 2-methyl-1-propenyl, 3-pentynyl, cyclopropylmethyl, cyclopentylmethyl, cyclohexylmethyl, 2-thienylmethyl, 3-thienylmethyl, benzyl phenethyl, 4-fluorobenzyl, 1-hydroxy-1-phenylmethyl, phenyl, 4-chlorophenyl, 4-fluorophenyl, 4-methoxyphenyl, 4-methlphenyl, 3-methoxyphenyl, 2-methoxyphenyl, and 4-dimethylaminophenyl;

Rb is selected from the group consisting of ethyl, n-propyl, n-butyl, 2-methoxyethyl, 3-methoxypropyl, 2-propenyl, 2-propynyl, 2-butynyl, cyclopropylmethyl, benzyl, 2,4-dimethoxybenzyl, 3-chlorobenzyl, 4-fluorobenzyl, 4-methoxybenzyl, 4- chlorobenzyl, 3-methoxybenzyl, 2-fluorobenzyl and 2-furylmethyl; and

Rc is hydrogen.

5. A compound as claimed in claim 1, 2, 5 or 6 wherein Rb is propyl, butyl or 2-propenyl.

6. A compound claimed in claim 1 wherein said pharmaceutically acceptable salt is selected from the group consisting of those made with hydrochloric, hydrobormic, sulfuric, nitric, phosphoric and methanesulfonic acids.

7. A pharmaceutical composition comprising a compound of claim 1 or a pharmaceutically acceptable salt thereof in an amount sufficient to reduce anxiety in a living mammal in need of such treatment in association with a non-toxic pharmaceutically acceptable diluent or carrier.

8. A method of treating anxiety in a living mammal comprising administering to the mammal an effective amount of a compound of claim 1 or a pharmaceutically acceptable salt thereof.

* * * * *